(12) United States Patent
McNaughton-Smith et al.

(10) Patent No.: US 7,205,307 B2
(45) Date of Patent: Apr. 17, 2007

(54) PYRIMIDINES AS NOVEL OPENERS OF POTASSIUM ION CHANNELS

(75) Inventors: Grant A. McNaughton-Smith, Morrisville, NC (US); George S. Amato, Cary, NC (US); Paul C. Fritch, Cary, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 10/305,706

(22) Filed: Nov. 27, 2002

(65) Prior Publication Data

US 2003/0181465 A1 Sep. 25, 2003

Related U.S. Application Data

(60) Provisional application No. 60/357,313, filed on Feb. 14, 2002.

(51) Int. Cl.
- C07D 239/26 (2006.01)
- C07D 239/30 (2006.01)
- A61K 31/505 (2006.01)
- A61P 25/08 (2006.01)
- A61P 29/00 (2006.01)
- C07D 239/34 (2006.01)
- C07D 239/52 (2006.01)

(52) U.S. Cl. ............... 514/256; 544/322; 544/324; 544/300; 544/301; 544/309; 544/310; 544/316; 544/319

(58) Field of Classification Search ......... 544/300, 544/301, 309, 310, 316, 319, 322, 334; 514/256, 514/269
See application file for complete search history.

(56) References Cited

U.S. PATENT DOCUMENTS

| | | | |
|---|---|---|---|
| 4,980,355 | A | 12/1990 | Zondler et al. |
| 5,811,428 | A | 9/1998 | Suto et al. |
| 5,849,789 | A | 12/1998 | Rostock et al. |
| 5,852,053 | A | 12/1998 | Rostock et al. |
| 6,372,767 | B1 | 4/2002 | McNaughton-Smith et al. |
| 6,469,042 | B1 | 10/2002 | Hewawasam et al. |

FOREIGN PATENT DOCUMENTS

| | | |
|---|---|---|
| EP | 0 554 543 B1 | 2/1996 |
| WO | WO 97/09315 A1 | 3/1997 |
| WO | WO-99041231 A1 * | 8/1999 |
| WO | WO 00/46203 A2 | 8/2000 |
| WO | WO 01/02354 A1 | 1/2001 |
| WO | WO 01/49685 A2 | 7/2001 |
| WO | WO 02/066036 A1 | 8/2002 |
| WO | WO 02/072088 A2 | 9/2002 |
| WO | WO-02070483 A1 * | 9/2002 |
| WO | WO 02/096858 A1 | 12/2002 |
| WO | WO-02098363 A2 * | 12/2002 |
| WO | WO-03037274 A2 * | 5/2003 |
| WO | WO-03068769 A1 * | 8/2003 |

OTHER PUBLICATIONS

Mulley et al. Curr. Opin. Neurol., 16(2): 171-176, 2003.*
Jensen BS CNS Drug Rev. 8(4): 353-360, 2002.*
Hashimoto et al. Chemical & Pharmaceutical Bulletin, 48(10). 1504-1513, 2000.*
Pie et al. Synthesis 7, 838-842, 1996.*
Machon et al. Polish Journal of Pharmacology and Pharmacy 28(1), 6-67, 1976.*
Gloria, T.S., Revista de Farmacia e Bioquimica da Universidade de Sao Paulo 9(1) 193-199, 1971.*
Wilczynska et al. Chemik, 18, 28-29, 1965.*
Wickenden et al., Expert. Opin. Ther. Patents 14(4); 1-12, 2004 . .*
Avramopoulos, D. et al.; "Linkage of bipolar affective disorder on chromosome 8q24: follow-up and parametric analysis"; *Molecular Psychiatry;* 2004; pp. 191-196; vol. 9, No. 2.
Browne, D. L. et al.; "Episodic ataxia/myokymia syndrome is associated with point mutations in the human potassium channel gene, KCNA1"; *Nature Genetics;* 1994; pp. 136-140; vol. 8, No. 2.
Cooper, E. C. et al.; "Colocalization and coassembly of two human brain M-type potassium channel subunits that are mutated in epilepsy"; *Proc. Natl. Acad. Sci. USA;* 2000; pp. 4914-4919; vol. 97, No. 9.
Cooper, E. C. et al.; "M Channel KCNQ2 subunits are localized to key sites for control of neuronal network oscillations and synchronization in mouse brain"; *The Journal of Neuroscience,* 2001; pp. 9529-9540; vol. 21.
Dedek, K. et al.; "Myokymia and neonatal epilepsy caused by a mutation in the voltage sensor of the KCNQ2 K+ channel"; *Proc. Natl. Acad. Sci. USA;* 2001; pp. 12272-12277; vol. 98, No. 21.
Dedek et al., Myokymia and neonatal epilepsy caused by a mutation in the voltage sensor of the KCNQ2 K+ channel. *Proc Natl Acad Sci U S A.* (2001) 98(21):12272-7.

(Continued)

Primary Examiner—Venkataraman Balasubramanian
(74) Attorney, Agent, or Firm—Townsend and Townsend and Crew LLP

(57) ABSTRACT

The present invention provides a genus of pyrimidine amides that are useful as openers of potassium ion channels. The compounds of the invention are of use in both therapeutic and diagnostic methods.

13 Claims, 6 Drawing Sheets

OTHER PUBLICATIONS

Goadsby P. J. et al.; "Migraine—current understanding and treatment"; *N. Engl. J. Med.;* Jan. 24, 2002; pp. 257-270; vol. 346, No. 4.

Ilyin, V. I. et al.; "Flupirtine—A positive modulator of heteromeric KCNQ2/Q3 channels"; *Soc. Neurosci. Abstract;* Program No. 758.10; 2002; Online Available Web Site: http://sfn.scholarone.com/itin2002/index.html Accessed on Feb. 28, 2004.

Kubisch, C. et al.; "KCNQ4, a novel potassium channel expressed in sensory outer hair cells, is mutated in dominant deafness"; *Cell;* 1999; pp. 437-446; vol. 96.

Saganich, M. J. et al.; "Differential expression of genes encoding subthreshold-operating voltage-gated K+ channels in brain"; *The Journal of Neuroscience;* 2001; pp. 4609-4624; vol. 21.

Schuster, G. et al.; "Flupirtine: A review of its neuroprotective and behavioural properties"; *CNS Drug Reviews;* 1998; pp. 149-164; vol. 4.

Smith J. S. et al.; "Differential expression of KCNQ2 splice variants: implications to M current function during neuronal development"; *The Journal of Neuroscience;* 2001; pp. 1096-1103; vol. 21, No. 4.

Falco, Elvira A., et al. "Studies on Condensed Pyrimidine Systems. X. Some 1,3-Oxazolo (5,4-d)pyrimidines", *Journal of the American Chemical Society,* (1952) 74(19):4897-4902.

\* cited by examiner (1)

(9)

(2)

(10)

(3)

(11)

(4)

(12)

(5)

(13)

(6)

(14)

(7)

(15)

(8)

(16)

(62)

(63)

(64)

(65)

(66)

(67)

(68)

(69)

(70)

(71)

(72)

(73)

(74)

(75)

(76)

(77)

(78)

(79)

(80)

(81)

(82)

(83)

(84)

(85)

(86)

(87)

(88)

(89)

(90)

(91)

(92)

PYRIMIDINES AS NOVEL OPENERS OF POTASSIUM ION CHANNELS

CROSS-REFERENCE TO RELATED APPLICATIONS

This is a non-provisional filing of U.S. provisional patent application No. 60/357,313, filed on Feb. 14, 2002, the disclosure of which is incorporated herein by reference in its entirety for all purposes.

FIELD OF THE INVENTION

This invention relates to the use of pyrimidines as potassium channel openers and to the treatment of diseases modulated by potassium channels. Additionally, this invention relates to novel pyrimidine compounds that are useful as potassium channel openers.

BACKGROUND OF THE INVENTION

Ion channels are cellular proteins that regulate the flow of ions, including calcium, potassium, sodium and chloride into and out of cells. These channels are present in all human cells and affect such physiological processes as nerve transmission, muscle contraction, cellular secretion, regulation of heartbeat, dilation of arteries, release of insulin, and regulation of renal electrolyte transport. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into at least 8 families, based on predicted structural and functional similarities (Wei et al., *Neuropharmacology* 35(7): 805–829 (1997)). Three of these families (Kv, eag-related, and KQT) share a common motif of six transmembrane domains and are primarily gated by voltage. Two other families/ also contain this motif but are gated by cyclic nucleotides (CNG) and calcium (small conductance and intermediate conductance potassium channels), respectively. The small conductance and intermediate conductance, calcium activated potassium channels comprise a family of calcium activated potassium channels gated solely by calcium, with a unit conductance of 2–20 and 20–85 pS, respectively. Macroscopic and unitary intermediate conductance, calcium activated potassium channel currents show inward rectification (see, e.g., Ishii et al., *Proc. Natl. Acad. Sci USA* 94: 11651–11656 (1997). The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066–71 (1997)) and are gated by both voltage and calcium or pH (Schreiber et al., *J. Biol. Chem.* 273: 3509–16 (1998)). Another family, the inward rectifier potassium channels (Kir), belongs to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625–633 (1996); Shi et al., *Neuron* 16(4): 843–852 (1996)). In another example, the KQT family beta subunit, minK, primarily changes activation kinetics (Sanguinetti et al., *Nature* 384: 80–83 (1996)).

Certain members of the Kv family of potassium channels were recently renamed (see Biervert, et al., *Science* 279: 403–406 (1998)). KvLQT1 was re-named KCNQ1, and the KvLQT1-related channels (KvLR1 and KvLR2) were renamed KCNQ2 and KCNQ3, respectively. More recently, a fourth member of the KCNQ subfamily was identified (KCNQ4) as a channel expressed in sensory outer hair cells (Kubisch, et al., *Cell* 96(3): 437–446 (1999)). KCNQ5 (Kananura et al., *Neuroreport* 11(9):2063 (2000)), and KCNQ 3/5 (Wickenden et al., *Br. J. Pharma* 132: 381 (2001)) has also recently been described.

KCNQ2 and KCNQ3 have been shown to be nervous system-specific potassium channels associated with benign familial neonatal convulsions ("BFNC"), a class of idiopathic generalized epilepsy (see, Leppert, et al., *Nature* 337: 647–648 (1989)). These channels have been linked to M-current channels (see, Wang, et al., *Science* 282: 1890–1893 (1998)). The discovery and characterization of these channels and currents provides useful insights into how these voltage dependent (Kv) potassium channels function in different environments, and how they respond to various activation mechanisms. Such information has now led to the identification of modulators of KCNQ2 and KCNQ3 potassium channels or the M-current, and the use of such modulators as therapeutic agents. The modulators are the subject of the present invention.

New classes of compounds that act to open potassium channels would represent a significant advance in the art and provide the opportunity to develop treatment modalities for numerous diseases associated with these channels. The present invention provides a new class of potassium channel opening compounds, methods of using the compounds and compositions containing them.

SUMMARY OF THE INVENTION

The present invention provides pyrimidines, prodrugs and pharmaceutically acceptable salts thereof ("compounds of the invention"), which are useful in the treatment of diseases through the modulation of potassium ion flux through voltage-dependent potassium channels.

The compounds of the invention have a structure according to Formula I:

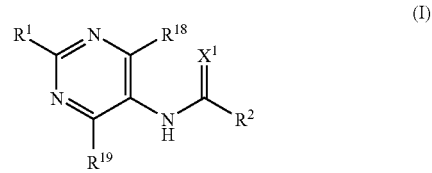

in which, $R^1$ represents a member selected from substituted or unsubstituted $(C_1–C_6)$alkyl, $(C_1–C_6)$alkoxy and halogen. The symbol $R^2$ represents a member selected from substituted or unsubstituted aryl, substituted or unsubstituted heteroaryl, and substituted or unsubstituted heterocycloalkyl. The symbols $R^{18}$ and $R^{19}$ represent members independently selected from H, cyano, substituted or unsubstituted ($C_1$–$C_6$)alkyl, substituted or unsubstituted ($C_1$–$C_6$) alkoxy, and halogen. $X^1$ is a member selected from O, S, and $NR^4$, in which $R^4$ is a member selected from H, $OR^{20}$, and substituted or unsubstituted ($C_1$–$C_6$)alkyl. $R^{20}$ represents H or substituted or unsubstituted ($C_1$–$C_6$) alkyl.

In yet another aspect, the present invention provides a method for modulating ion flux through voltage dependent potassium channels, comprising contacting a cell containing the target ion channels with a compound according to Formula I.

In still another aspect, the present invention provides a method for the treatment of diseases through modulation of ion flux through voltage dependent potassium channels, the method comprising treating the host with an effective amount of a potassium channel opening compound of Formula I.

In another aspect the present invention also provides pharmaceutical compositions comprising one or more compounds of Formula I in admixture with pharmaceutically acceptable excipients.

These and other objects aspects and advantages of the invention will be apparent from the detailed description that follows.

DETAILED DESCRIPTION OF THE INVENTION AND THE PREFERRED EMBODIMENTS

Abbreviations and Definitions

Figure 1A:
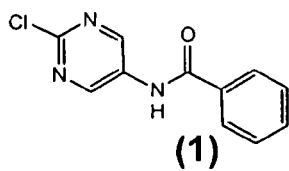
FIG. 1 displays structures of representative compounds of the invention.

The abbreviations used herein have their conventional meaning within the chemical and biological arts. For example: CHO, Chinese hamster ovary; EBSS, Earl's Balanced Salt Solution; KCNQ, potassium channel Q; KCNQ2, potassium channel Q2, hSK, $Ca^{2+}$ activated small conductance potassium channels; SDS, sodium dodecyl sulfate; $Et_3N$, triethylamine; MeOH, methanol; and DMSO, dimethylsulfoxide.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$–$C_4$)alkoxy, and fluoro($C_1$–$C_4$)alkyl, in a number ranging from zero to the total number of open valences on the aromatic ring system; and where R', R", R'" and R"" are preferably independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine*, pp. 93–98 (Wilson et al., eds., 12th ed. 1991); Williams et al., *J. of Medicinal Chem.* 42:1481–1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

Introduction

The present invention provides compounds that, inter alia, are useful in the treatment of diseases through the modulation of potassium ion flux through voltage-dependent potassium channels. More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases), and as neuroprotective agents (e.g., to prevent stroke and the like). Compounds of the invention have use as agents for treating convulsive states, for example that following grand mal, petit mal, psychomotor epilepsy or focal seizure. The compounds of the invention are also useful in treating disease states such as gastroesophogeal reflux disorder and gastrointestinal hypermotility disorders.

Moreover, compounds of the invention are useful in the treatment of pain, for example, neuropathic pain, inflammatory pain, cancer pain, migraine pain, and musculoskeletal pain. The compounds are also useful to treat conditions, which may themselves be the origin of pain, for example, inflammatory conditions, including arthritic conditions (e.g., rheumatoid arthritis, rheumatoid spondylitis, osteoarthritis and gouty arthritis) and non-articular inflammatory conditions (e.g., herniated, ruptured and prolapsed disc syndrome, bursitis, tendonitis, tenosynovitis, fibromyalgia syndrome, and other conditions associated with ligamentous sprain and regional musculoskeletal strain). Particularly preferred compounds of the invention are less ulcerogenic than other anti-inflammatory agents (e.g., ibuprofen, naproxen and aspirin). Furthermore, the compounds of the invention are useful in treating conditions and pain associated with abnormally raised skeletal muscle tone.

The compounds of the invention are also of use in treating anxiety (e.g. anxiety disorders). Anxiety disorders are defined in the Diagnostic and Statistical Manual of Mental Disorders (Third Edition-revised 1987, published by the American Psychiatric Association, Washington, D.C., see, pages 235 to 253), as psychiatric conditions having symptoms of anxiety and avoidance behavior as characteristic features. Included amongst such disorders are generalized anxiety disorder, simple phobia and panic disorder.

Anxiety also occurs as a symptom associated with other psychiatric disorders, for example, obsessive compulsive disorder, post-traumatic stress disorder, schizophrenia, mood disorders and major depressive disorders, and with organic clinical conditions including, but not limited to, Parkinson's disease, multiple sclerosis, and other physically incapacitating disorders.

The development of therapeutic agents, which act on potassium ion channels has received considerable recent attention. One group has described a family of N-alkyl benzamides that act by blocking potassium channels (see, PCT/US98/02364, published as WO 98/37068). In contrast, the pyrimidine amides provided herein act by opening potassium channels.

In view of the above-noted discovery, the present invention provides compounds, compositions, and methods for increasing ion flux in voltage-dependent potassium channels, particularly, though not necessarily limited to, those channels responsible for the M-current, that is to say, the compounds, compositions and methods of the invention can also serve to act as agonists for other potassium channels, particularly those of the KCNQ family, e.g., KCNQ2, KCNQ3, KCNQ4 and KCNQ5 channels as well as the heteromultimer channels such as KCNQ2/3, KCNQ3/5. As used herein, the term "M-current," "channels responsible for the M-current" and the like, refers to a slowly activating, non-inactivating, slowly deactivating voltage-gated $K^+$ channel. M-current is active at voltages close to the threshold for action potential generation in a wide variety of neuronal cells, and thus, is an important regulator of neuronal excitability.

Recently, members of the voltage-dependent potassium channel family were shown to be directly involved in diseases of the central or peripheral nervous system. The pyrimidine amides provided herein are now shown to act as potassium channel openers and to be of use in treating diseases in which a voltage-dependent potassium channel is implicated.

Description of the Embodiments

I. Activators of Voltage-Dependent Potassium Channels

The present invention provides, in one aspect, compounds according to Formula I:

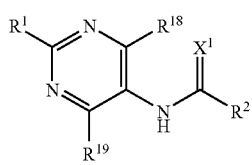

in which, $R^1$ represents a member selected from substituted or unsubstituted $(C_1-C_6)$alkyl, $(C_1-C_6)$alkoxy and halogen. The symbol $R^2$ represents a member selected from substituted or unsubstituted aryl, substituted or unsubstituted heteroaryl, and substituted or unsubstituted heterocycloalkyl. The symbols $R^{18}$ and $R^{19}$ represent members independently selected from H, cyano, substituted or unsubstituted $(C_1-C_6)$alkyl, substituted or unsubstituted $(C_1-C_6)$ alkoxy, and halogen. $X^1$ is a member selected from O, S, and $NR^4$, in which $R^4$ is a member selected from H, $OR^{20}$, and substituted or unsubstituted $(C_1-C_6)$alkyl. $R^{20}$ represents H or substituted or unsubstituted $(C_1-C_6)$ alkyl.

In an exemplary embodiment, $R^1$ is a member selected from the group consisting of $CH_3$, $CF_3$, $OCH_3$ F, Br and Cl. In another exemplary embodiment, $X^1$ is O.

As discussed above, $R^2$ can be any heterocycle or heteroaromatic ring system. In exemplary embodiments, $R^2$ is a member selected from the group consisting of substituted or unsubstituted phenyl, substituted or unsubstituted indolyl, substituted or unsubstituted benzofuranyl, substituted or unsubstituted furanyl, substituted or unsubstituted thienyl, substituted or unsubstituted isothiazolyl, substituted or unsubstituted benzopyrazole, substituted or unsubstituted oxazole, substituted or unsubstituted triazole, substituted or unsubstituted thiadiazole, substituted or unsubstituted pyrazolyl, substituted or unsubstituted pyrimidine, and substituted or unsubstituted pyrazine.

In another exemplary embodiment, $R^2$ is a substituted phenyl according to Formula II:

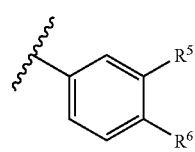

in which, the symbols $R^5$ and $R^6$ independently represent halogen, substituted or unsubstituted phenyl, substituted or unsubstituted $(C_1-C_6)$alkyl, cyano, nitro, $-NR^7R^8$, $-S(O)_nR^7$, $-OR^7$, or $-SO_2NR^7R^8$. The symbols $R^7$ and $R^8$ independently represent hydrogen, substituted or unsubstituted $(C_1-C_8)$alkyl, substituted or unsubstituted alkylaryl, substituted or unsubstituted alkylheteroaryl, substituted or unsubstituted cycloalkyl, substituted or unsubstituted heteroalkyl, substituted or unsubstituted heterocycloalkyl, substituted or unsubstituted aryl, substituted or unsubstituted heteroaryl, or substituted or unsubstituted aryl$(C_1-C_4)$alkyl. $R^5$ and $R^6$, together with the atoms to which they are attached are optionally joined to form a 5- to 7-membered cycloalkyl or heterocycloalkyl ring system. $R^7$ and $R^8$ are optionally combined with the nitrogen to which each is attached to form a 5-, 6- or 7-membered ring optionally having additional heteroatoms at the ring vertices. The symbol n is an integer from 0 to 2, and when n is 1 or 2, $R^7$ is other than H.

In an exemplary embodiment of a compound of the invention in which $R^2$ has a structure according to Formula II, $R^5$ and $R^6$ are preferably independently selected from H, F, Cl, Br, $CH_3$, $CH_2NR^7R^8$, $CH_2SR^7$, $CH_2SO_2R^7$, $NR^7R^8$, $(C_3-C_8)$heteroalkyl, $(C_3-C_8)$heteroaryl, $SR^7$, $SO_2R^7$, $OR^7$ and $CF_3$.

In a still further embodiment, $R^2$ has the structure according to Formula III:

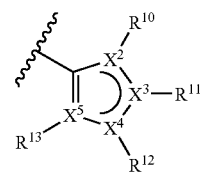

in which, the curved line in the ring system represents a π bond formed between $X^3$ and $X^2$ or $X^3$ and $X^4$. The symbols $X^2$, and $X^4$ represent groups that are independently selected from C, O, S, and N. $X^3$, and $X^5$ are independently N or C. The radicals represented by the symbols $R^{10}$, $R^{11}$, $R^{12}$ and $R^{13}$ are either present or absent as necessary to satisfy, but not exceed the valence of the atom to which they are attached. $R^{10}$, $R^{11}$, $R^{12}$ and $R^{13}$ are independently selected from hydrogen, halogen, substituted or unsubstituted phenyl, substituted or unsubstituted $(C_1-C_6)$alkyl, cyano, nitro, $-NR^7R^8$, $-S(O)_nR^7$, $-OR^7$ and $-SO_2NR^7R^8$. Two or more members selected from the group of $R^{10}$, $R^{11}$, $R^{12}$ and $R^{13}$ are optionally combined to form a 5-, 6- or 7-membered ring optionally having additional heteroatoms at the ring vertices. The symbols $R^7$ and $R^8$ independently represent the radicals hydrogen, substituted or unsubstituted ($C_1$–$C_8$) alkyl, substituted or unsubstituted alkylaryl, substituted or unsubstituted alkylheteroaryl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted aryl($C_1$–$C_4$)alkyl. $R^7$ and $R^8$ are optionally combined with the nitrogen to which each is attached to form a 5-, 6- or 7-membered ring optionally having additional heteroatoms at the ring vertices. The symbol n represents an integer from 0 to 2.

In yet another exemplary embodiment, $R^2$ has the structure according to Formula IV:

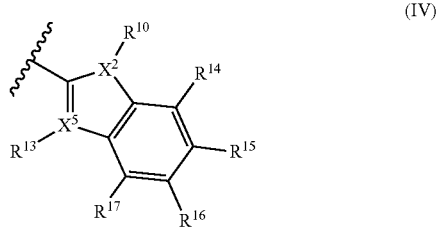

(IV)

in which $X^2$ represents O, S, N or C. $X^5$ represents N or C. $R^{10}$, and $R^{13}$ are either present or absent as necessary to satisfy, but not exceed the valence of the atom to which they are attached and are members independently selected from, hydrogen, hydroxyl, halogen, substituted or unsubstituted aryl, substituted or unsubstituted heteroaryl, substituted or unsubstituted ($C_1$–$C_6$)alkyl, cyano, nitro, —$NR^7R^8$, —$S(O)_nR^7$, —$OR^7$ and —$SO_2NR^7R^8$. $R^{14}$, $R^{15}$, $R^{16}$ and $R^{17}$ represent radicals that are independently selected from hydrogen, hydroxyl, halogen, substituted or unsubstituted aryl, substituted or unsubstituted heteroaryl, substituted or unsubstituted ($C_1$–$C_6$)alkyl, cyano, nitro, —$NR^7R^8$, —$S(O)_nR^7$, —$OR^7$ and —$SO_2NR^7R^8$. $R^7$ and $R^8$ are each independently selected from hydrogen, ($C_1$–$C_8$)alkyl, substituted ($C_1$–$C_8$)alkyl, substituted or unsubstituted alkylaryl, substituted or unsubstituted alkylheteroaryl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted aryl($C_1$–$C_4$)alkyl. $R^7$ and $R^8$ are optionally combined with the nitrogen to which each is attached to form a 5-, 6- or 7-membered ring optionally having additional heteroatoms at the ring vertices. The symbol n represents an integer from 0 to 2.

In a preferred embodiment, the symbols $R^{14}$, $R^{15}$, $R^{16}$, and $R^{17}$ independently represent a radical selected from H, halogen, $CF_3$, and substituted or unsubstituted ($C_1$–$C_4$) alkyl.

Figure 1A:
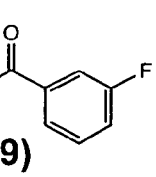
Figure 1A:
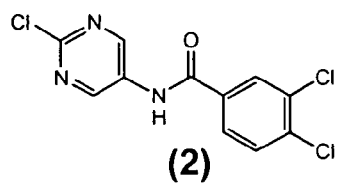
Figure 1A:
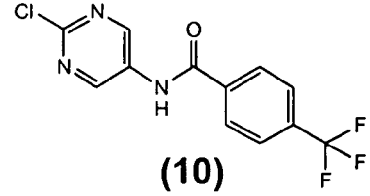
Figure 1A:
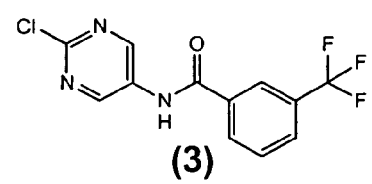
Figure 1A:
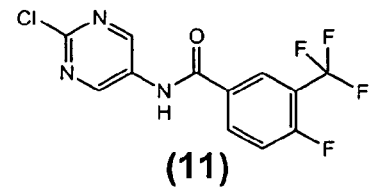
Figure 1A:
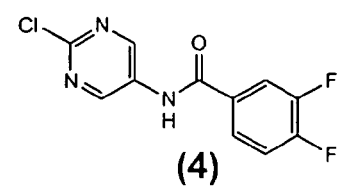
Figure 1A:
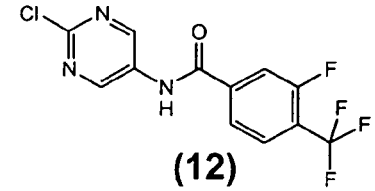
Figure 1A:
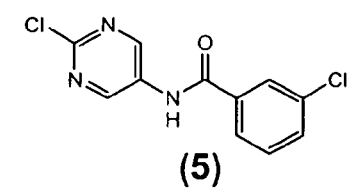
Figure 1A:
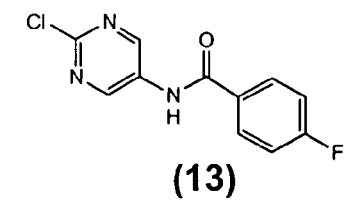
Figure 1A:
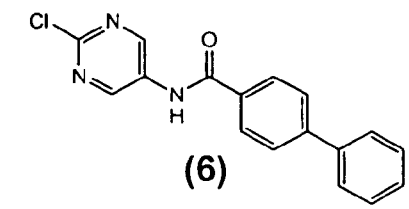
Figure 1A:
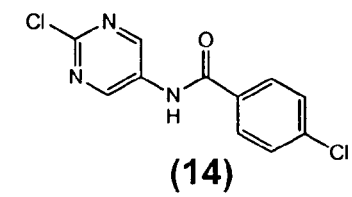
Figure 1A:
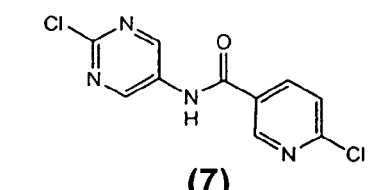
Figure 1A:
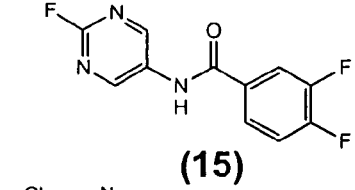
Figure 1A:
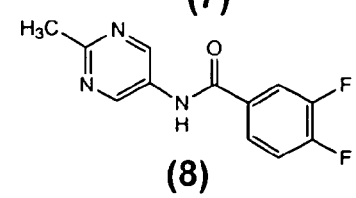
Figure 1A:
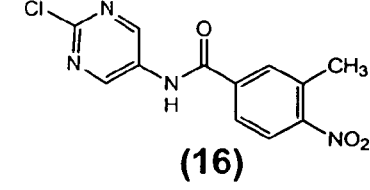
Figure 1B:
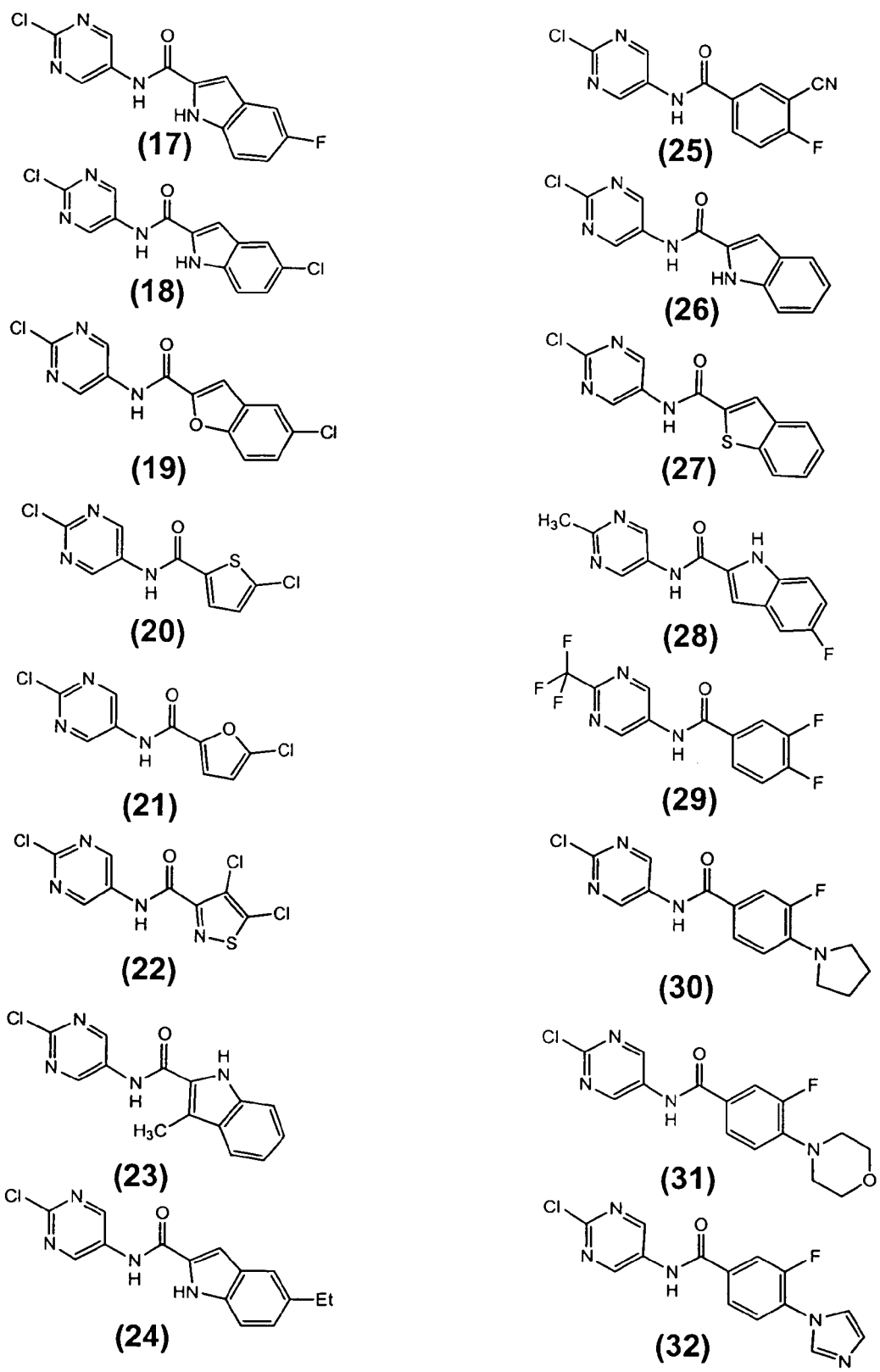
Figure 1C:
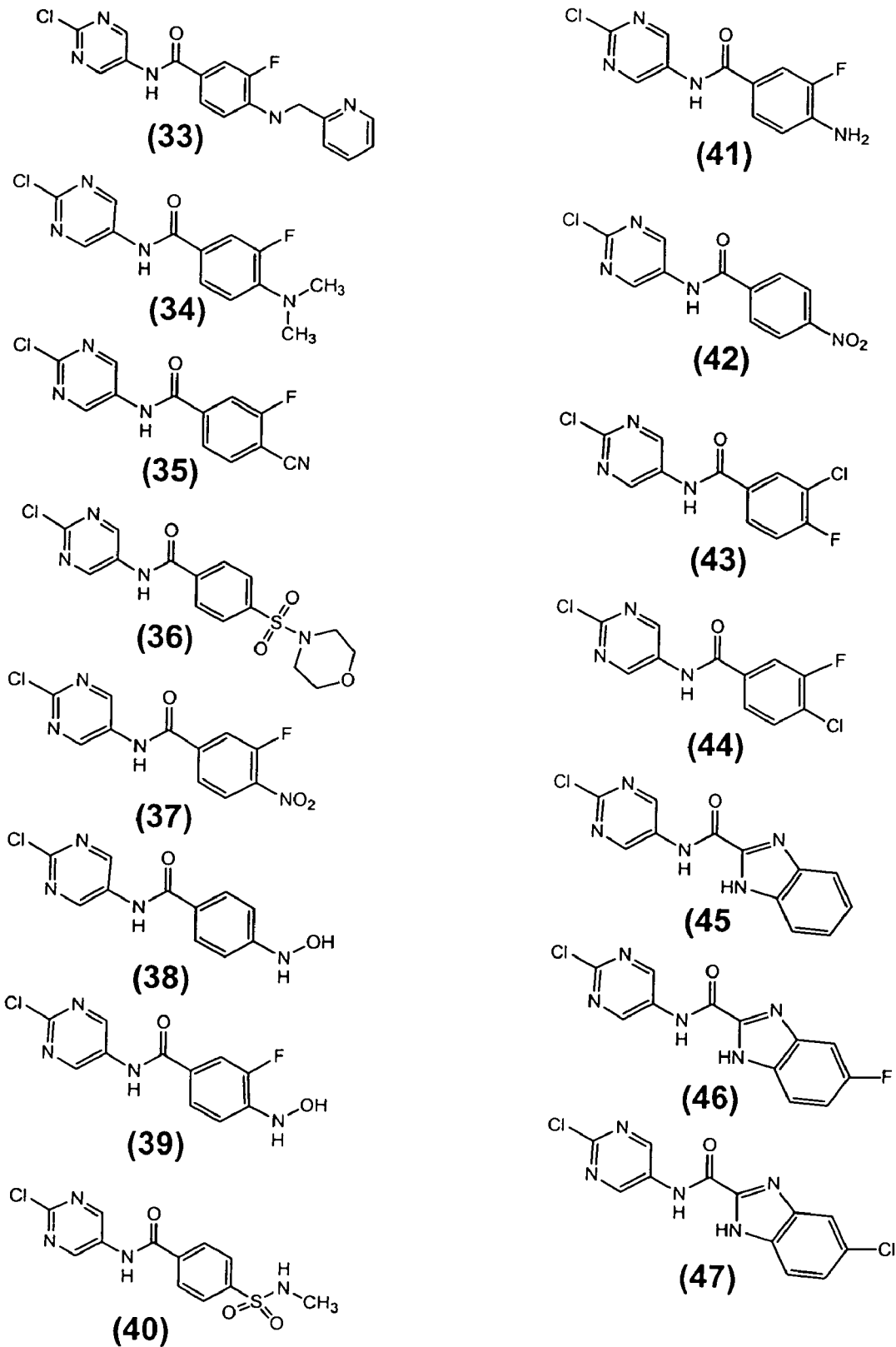
Figure 1D:
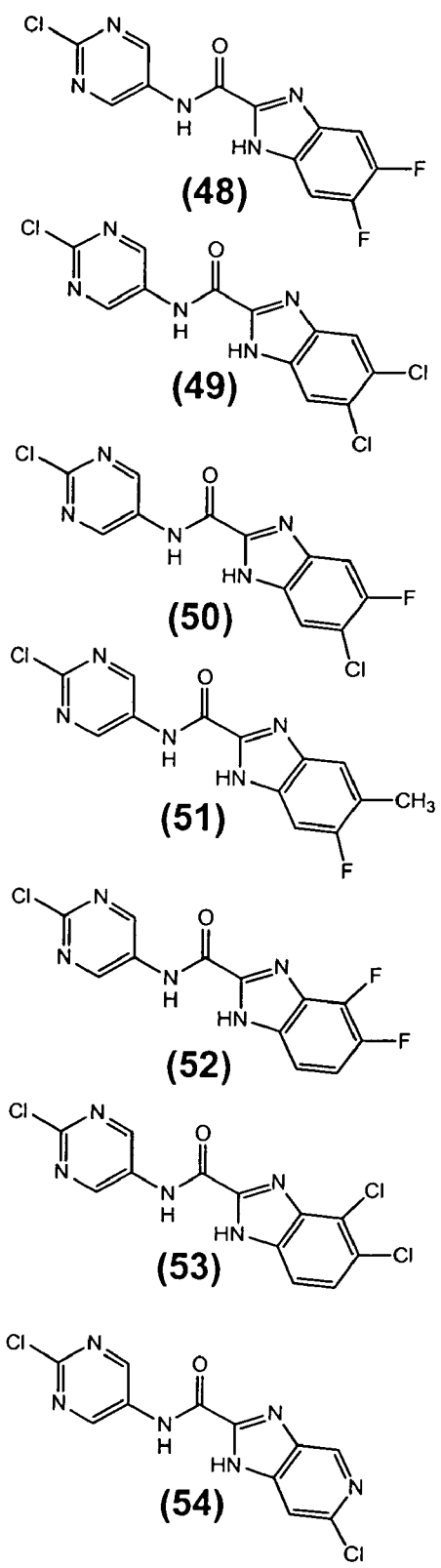
Figure 1D:
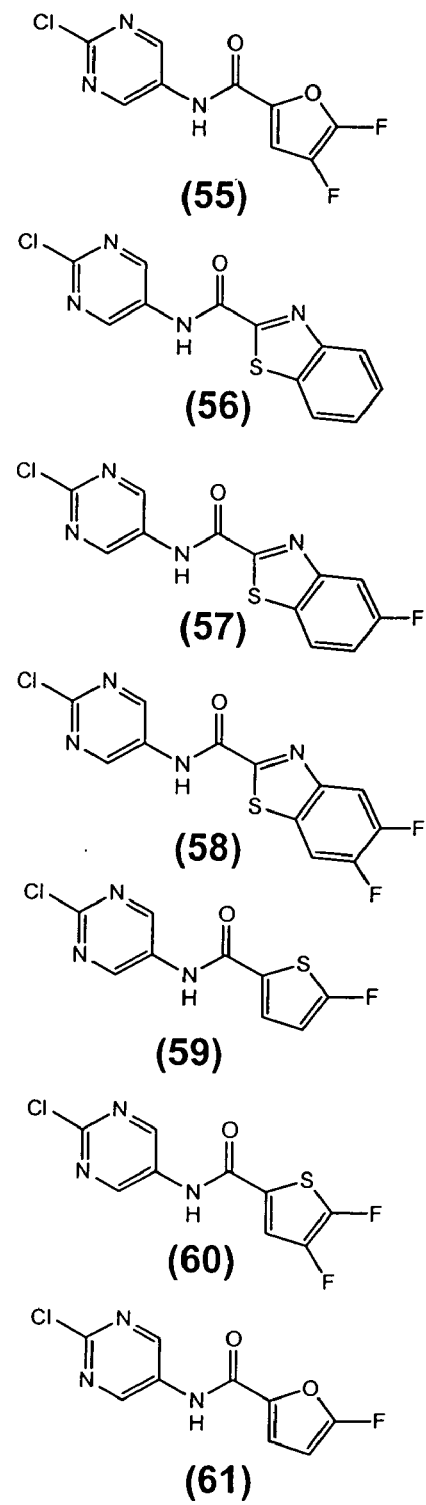
Figure 1E:
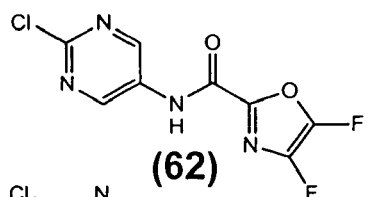
Figure 1E:
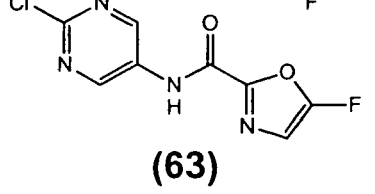
Figure 1E:
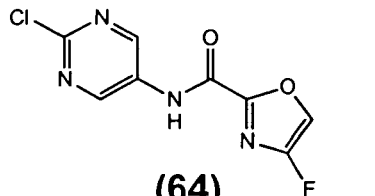
Figure 1E:
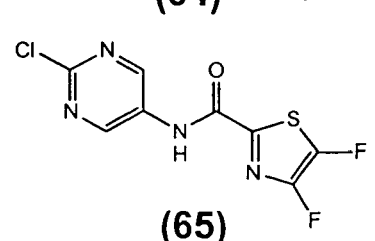
Figure 1E:
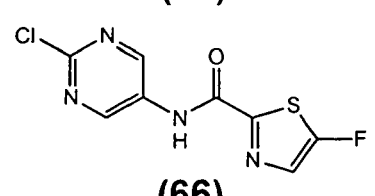
Figure 1E:
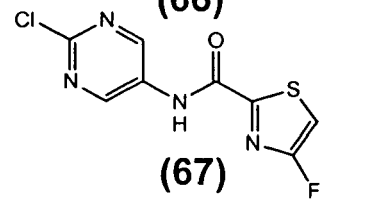
Figure 1E:
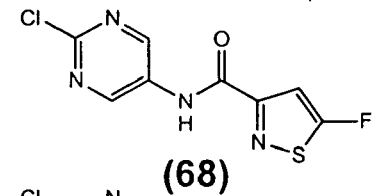
Figure 1E:
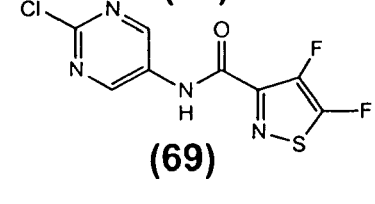
Figure 1E:
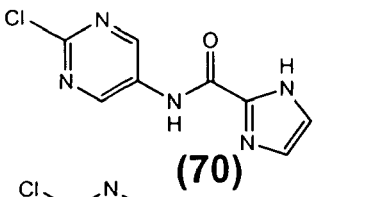
Figure 1E:
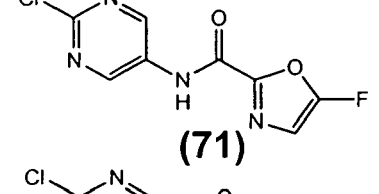
Figure 1E:
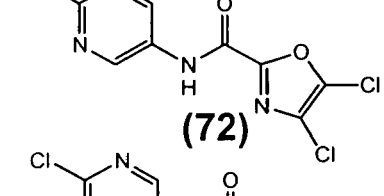
Figure 1E:
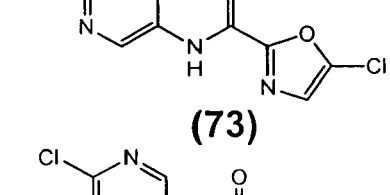
Figure 1E:
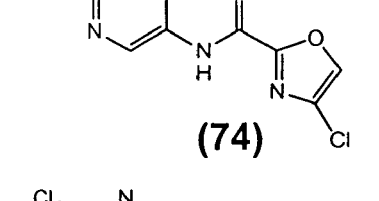
Figure 1E:
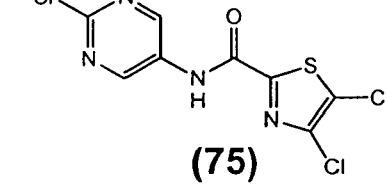
Figure 1E:
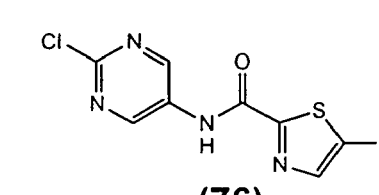
Figure 1E:
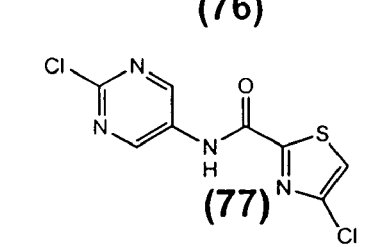
Figure 1F:
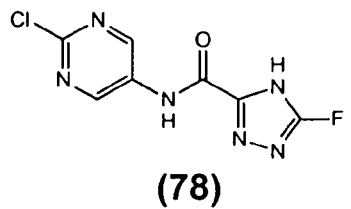
Figure 1F:
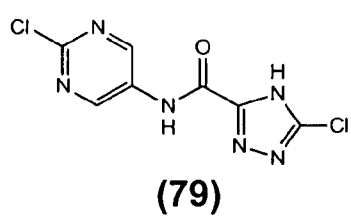
Figure 1F:
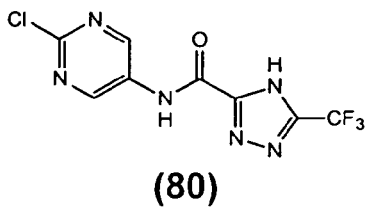
Figure 1F:
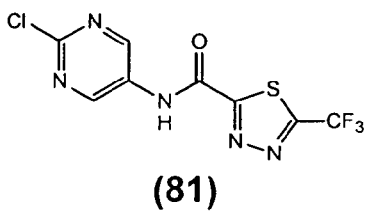
Figure 1F:
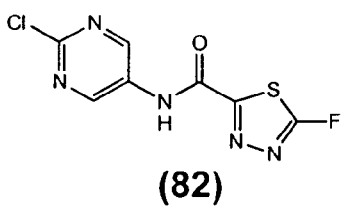
Figure 1F:
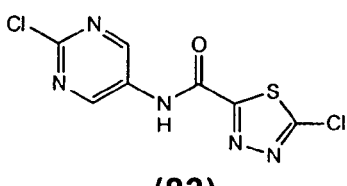
Figure 1F:
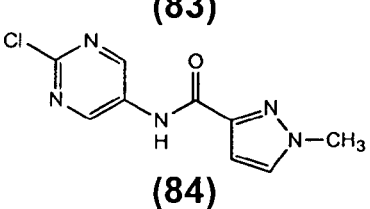
Figure 1F:
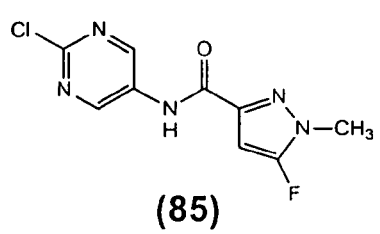
Figure 1F:
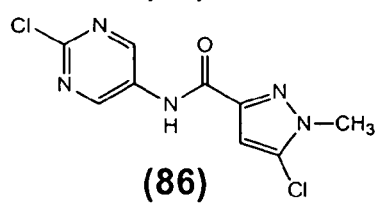
Figure 1F:
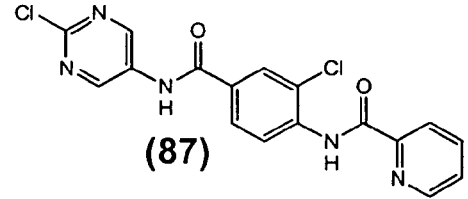
Figure 1F:
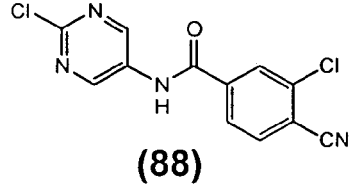
Figure 1F:
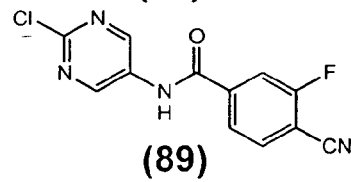
Figure 1F:
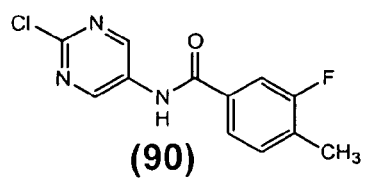
Figure 1F:
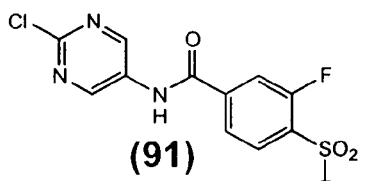
Figure 1F:
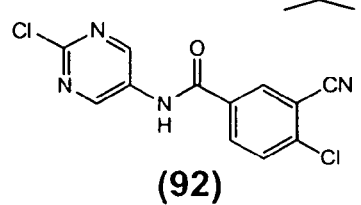

Certain combinations of the above embodiments form a group of preferred compounds. Accordingly, representative preferred compounds of the present invention are set forth in FIG. 1, appended hereto.

Also within the scope of the present invention are compounds of the invention that function as poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or reactive analogues thereof are attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formulae I–IV, which are functionalized to afford compounds having a water-solubility that is enhanced relative to analogous compounds that are not similarly functionalized. Methods of enhancing the water-solubility of organic compounds is known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Preparation of Potassium Channel Openers

Compounds of the nature described herein can be prepared following the route outlined in Scheme 1.

Scheme 1

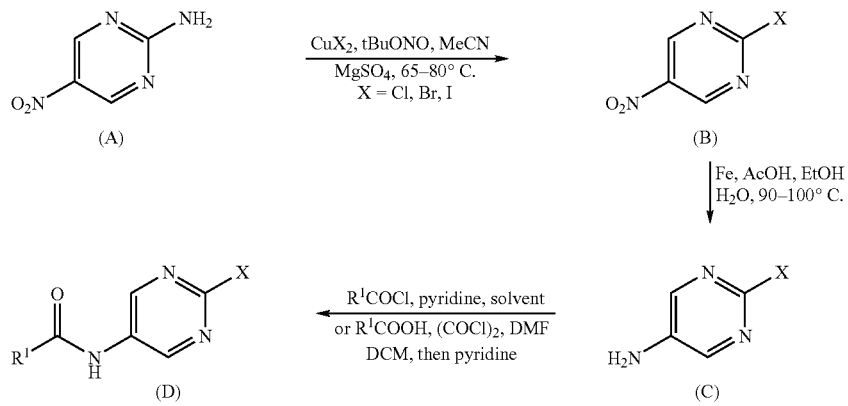

In Scheme 1, the 2-aminopyrimidine (A) is converted to a 2-halopyrimidine (B), via the corresponding diazonium intermediate, using t-butylnitrite and a copper halide. Selective reduction of the nitro group with iron in the presence of acetic acid affords the corresponding aniline (C). Coupling of (C) with an activated carboxylic acid derivative generates the desired compounds (D).

The pyrimidine ring can be further elaborated. For example, 2-methylpyrimidine amides are synthesized from the corresponding 2-chloropyrimidine amides utilizing standard Suzuki type cross coupling conditions as shown in Scheme 2.

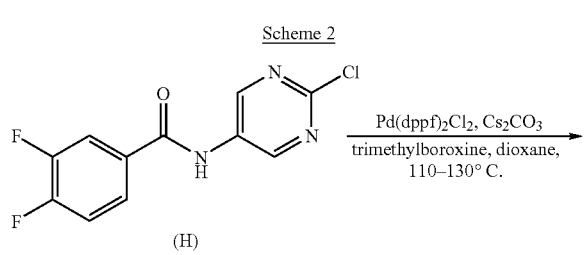

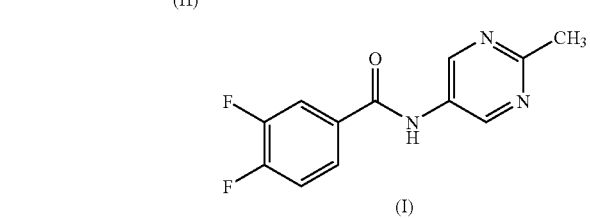

Compounds of the invention in which X is halogen, e.g., chloro, can also be prepared following the route outlined in Scheme 3. 2-Hydroxypyrimidine (J) is nitrated selectively in the 5-position using a mixture of sulfuric and nitric acids at elevated temperatures. The hydroxyl of compound (K) is then converted to the chloro-derivative (L) using phosphorous oxychloride. The nitro functionality of compound (M) is reduced and, optionally, further elaborated using the conditions such as those outlined in Scheme 1 to generate the desired compounds. The example shown depicts the elaboration to generate compound 4.

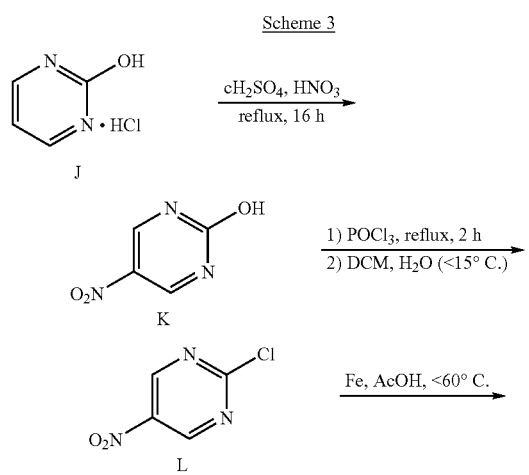

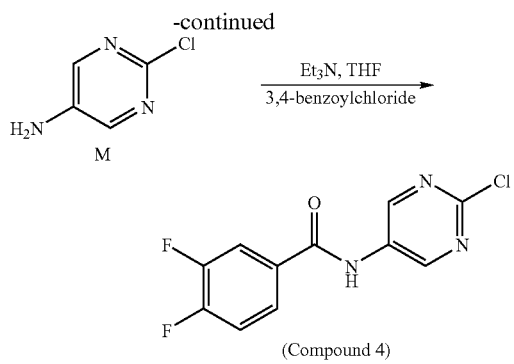

Sulfone substituted compounds of the invention are readily prepared by methods such as that set forth in Scheme 4. In Scheme 4, the para-fluoro of 3,4-difluorobenzoic acid is selectively displacing using a sulfide and cesium carbonate in a polar solvent at elevated temperatures. The resulting acid is then be coupled to an aniline via the corresponding acid chloride. Selective oxidation of the sulfide to the sulfone was achieved with 3-chloroperbenzoic acid.

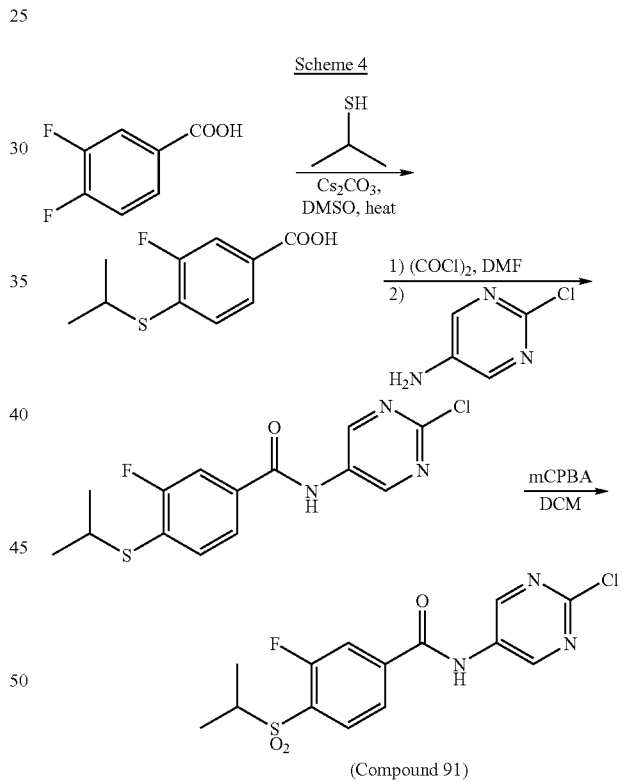

Other methods of preparing the pyrimidine amides of the invention will be apparent to, and are readily accessible by those of skill in the art.

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or hetero-dimeric species. Alternatively, the isothiocyanate is coupled with an amine-containing backbone, such as polylysine, thereby forming a conjugate between a polyvalent framework and a compound of the invention. If it is desired to prepare a hetereofuntionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Modulators of KCNQ Channels

Assays for determining the ability of a compound of the invention to open a potassium ion channel are generally known in the art. One of skill in the art is able to determine an appropriate assay for investigating the activity of a selected compound of the invention towards a particular ion channel. For simplicity, portions of the following discussion focuses on KCNQ2 as a representative example, however, the discussion is equally applicable to other potassium ion channels.

KCNQ monomers as well as KCNQ alleles and polymorphic variants are subunits of potassium channels. The activity of a potassium channel comprising KCNQ subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for activators of channels comprising KCNQ. As discussed elsewhere herein, activators (openers) of a potassium channel are useful for treating various disorders attributable to potassium channels. Such modulators are also useful for investigation of the channel diversity provided by KCNQ and the regulation/modulation of potassium channel activity provided by KCNQ.

Putative modulators of the potassium channels are tested using biologically active KCNQ, either recombinant or naturally occurring, or by using native cells, like cells from the nervous system expressing the M-current. KCNQ can be isolated, co-expressed or expressed in a cell, or expressed in a membrane derived from a cell. In such assays, KCNQ2 is expressed alone to form a homomeric potassium channel or is co-expressed with a second subunit (e.g., another KCNQ family member, preferably KCNQ3) so as to form a heteromeric potassium channel. Modulation is tested using one of the in vitro or in vivo assays described above. Samples or assays that are treated with a potential potassium channel activator are compared to control samples without the test compound, to examine the extent of modulation. Control samples (untreated with activators) are assigned a relative potassium channel activity value of 100. Activation of channels comprising KCNQ2 is achieved when the potassium channel activity value relative to the control is 110%, more preferably 130%, more preferably 170% higher. Compounds that increase the flux of ions will cause a detectable increase in the ion current density by increasing the probability of a channel comprising KCNQ2 being open, by decreasing the probability of it being closed, by increasing conductance through the channel, and/or increasing the number or expression of channels.

Changes in ion flux may be assessed by determining changes in polarization (i.e., electrical potential) of the cell or membrane expressing the potassium channel comprising, for example, KCNQ2, KCNQ2/3 or the M-current. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336:1575–1595 (1997)). Whole cell currents are conveniently determined using the standard methodology (see, e.g., Hamil et al., *Pflugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67–75 (1988); Daniel et al., *J. Pharmacol. Meth.* 25:185–193(1991); Holevinsky et al., *J. Membrane Biology* 137:59–70 (1994)). Assays for compounds capable of increasing potassium flux through M-current channels found in native cells or through the channel proteins comprising KCNQ2 or heteromultimers of KCNQ subunits can be performed by application of the compounds to a bath solution in contact with and comprising cells having a channel of interest (see, e.g., Blatz et al., *Nature* 323: 718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

KCNQ2 orthologs will generally confer substantially similar properties on a channel comprising such KCNQ2, as described above. In a preferred embodiment, the cell placed in contact with a compound that is suspected to be a KCNQ2 homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to KCNQ2 are considered homologs or orthologs of KCNQ2.

Utilizing screening assays such as described above, compounds of the invention were tested for their ability to open voltage-gated potassium channels. The results of these assays are set forth in Table 1 in which the data are presented in terms of relative potency of the compounds tested to one another. The compound numbers in Table 1 are cross-referenced to the compounds displayed in FIG. 1.

TABLE 1

| Compound ID # | Assay Activity |
|---|---|
| 3 | + |
| 4 | ++ |
| 5 | + |
| 8 | + |
| 9 | + |
| 20 | ++ |
| 44 | +++ |
| 90 | ++ |
| 91 | + |

+ indicates 10 µM > EC50 > 1 µM;
++ indicates 1 µM > EC50 > 0.5 µM; and
+++ indicates EC50 < 0.5 µM,
each in the test assay chosen for cells expressing voltage gated $K^+$ channels III. Pharmaceutical Compositions of Potassium Channel Openers In another aspect, the present invention provides pharmaceutical compositions comprising a pharmaceutically acceptable excipient and a compound according to the Formulae set forth above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

IV. Methods for Increasing Ion Flow in Voltage-Dependent potassium Channels

In yet another aspect, the present invention provides methods for increasing ion flow through voltage dependent potassium channels in a cell, comprising contacting a cell containing the target ion channels with a compound of Formula I, above.

The methods provided in this aspect of the invention are useful for the diagnosis of conditions that can be treated by modulating ion flux through voltage-dependent potassium channels, or for determining if a patient will be responsive to therapeutic agents which act by opening potassium channels. In particular, a patient's cell sample can be obtained and contacted with a compound of Formula I and the ion flux can be measured relative to a cell's ion flux in the absence of a compound of Formula I. An increase in ion flux will typically indicate that the patient will be responsive to a therapeutic regimen of ion channel openers.

V. Methods for Treating Conditions Mediated by Voltage-Dependent Potassium Channels In still another aspect, the present invention provides a method for the treatment of diseases or conditions mediated, at least in part, by voltage-dependent potassium channels. In this method, a subject suffering from such a condition or disease is administered an effective amount of a compound of Formula I.

The compounds provided herein are useful as potassium channel openers and find therapeutic utility via modulation of voltage-dependent potassium channels in the treatment of diseases or conditions. The potassium channels that are typically opened are described herein as voltage-dependent potassium channels such as the KCNQ potassium channels. As noted above, these channels may include homomultimers and heteromultimers of KCNQ2, KCNQ3, KCNQ4 and KCNQ5 or may include such genes or channels which exist in native cells or tissues and which are determined to be native M-current. A heteromultimer of two proteins, e.g., KCNQ2 and KCNQ3 is referred to as, for example, KCNQ2/3. The conditions that can be treated with the compounds and compositions of the present invention may include, but are not limited to, central or peripheral nervous system disorders (e.g., pain, migraine, ataxia, Parkinson's disease, bipolar disorders, spasticity, mood disorders, brain tumors, psychotic disorders, myokymia, seizures, epilepsy, hearing and vision loss, Alzheimer's disease, age-related memory loss, learning deficiencies, and motor neuron diseases, and as neuroprotective agents (e.g., to prevent stroke and the like)).

The compounds, compositions and methods of the present invention are of particular use in treating pain, including both inflammatory and neuropathic pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Examples of pain treated by a compound of the invention include, postoperative pain, osteoarthritis pain, pain associated with metastatic cancer, trigeminal neuralgia, glossopharangyl neuralgia, adiposis dolorosa, burn pain, acute herpetic and postherpetic neuralgia, diabetic neuropathy, occipital neuralgia, reflex sympathetic dystrophy, fibromyalgia, gout, burn pain, pain following stroke, thalamic lesions and other forms of neuralgic, neuropathic, and idiopathic pain syndromes (i.e., syndromes of pain of unknown origin as, for example, phantom limb pain).

In therapeutic use for the treatment of the above conditions, the compounds utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

The materials, methods and devices of the present invention are further illustrated by the examples, which follow. These examples are offered to illustrate, but not to limit the claimed invention.

EXAMPLES

General

In the examples below, unless otherwise stated, temperatures are given in degrees Celsius (° C.); operations were carried out at room or ambient temperature, "rt," or "RT," (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

General Experimental

Unless otherwise specified, all solvents (HPLC grade) and reagents were purchased from suppliers and used without further purification. Reactions were conducted under a blanket of argon unless otherwise stated. Analytical thin layer chromatography (tlc) was performed on Whatman Inc. 60 silica gel plates (0.25 mm thickness). Compounds were visualized under UV lamp (254 nM) or by developing with $KMnO_4$/KOH, ninhydrin or Hanessian's solution. Flash chromatography was done using silica gel from Selectro Scientific (particle size 32–63). $^1$H NMR, 19F NMR and $^{13}$C NMR spectra were recorded on a Varian 300 machine at 300 MHz, 282 MHz and 75.7 MHz, respectively. Melting points were recorded on a Electrothermal IA9100 apparatus and were uncorrected.

Example 1

Preparation of 2-chloro-5-nitro-pyrimidine

5-Nitro-pyrimidin-2-ylamine (A) (0.98 g, 7 mmol, 1 eq) was added to a stirring mixture of anhydrous copper (II) chloride (1.12 g, 8.4 mmol, 1.2 eq), tert-butylnitrite (1.24 mL, 10.5 mmol, 1.5 eq) and $MgSO_4$ (~300 mg) in acetonitrile (40 mL) at 65–80° C. (bath temperature). After 30 min the mixture was cooled to rt and diethyl ether (100 mL) was added. The organic layer was separated and washed sequentially with 1N aqueous HCl (2×20 mL), $H_2O$ (50 mL) and brine (20 mL). The organic layer was dried ($Na_2SO_4$) and concentrated under reduced pressure. Column chromatography of the crude material (hexanes/diethyl ether: 3:1) gave the desired product as a pale yellow solid (0.56 g, 50%).

Preparation of 2-chloro-pyrimidin-5-ylamine

Iron (3.38 g, 60 mmol) was added to a boiling solution of 2-chloro-5-nitro-pyrimidine (2.4 g, 15 mmol) in ethanol (40 mL), $H_2O$ (20 mL) and acetic acid (5 mL). The mixture was heated at reflux for a further 20 min then cooled to rt and neutralized with saturated aqueous sodium bicarbonate. EtOAc (100 mL) was added and the mixture was filtered through a pad of celite. The filtrate was washed with $H_2O$ (50 mL) and brine (20 mL). The organic layer was dried ($Na_2SO_4$) and concentrated under reduced pressure. Column chromatography of the crude material (hexanes/EtOAc: 1:1 to 1:2) gave the desired product as a yellow solid (0.74 g, 38%).

Example 2

Preparation of N-(2-chloro-pyrimidin-5-yl)-arylamides

2.1 General Method When X=Cl

Aryl acid chloride (1.1 eq) in THF (0.2 M) was added to a solution of 2-chloro-pyrimidin-5-ylamine (1 eq) and pyridine (1.2 eq) in THF (0.2M) at rt. After 1 h the suspension was diluted with EtOAc (5 mL/mmol), washed with $H_2O$ (20 mL) and dried ($Na_2SO_4$). Concentration under reduced pressure followed by column chromatography (hexanes/EtOAc) gave the desired products in high yields (>80%) typically as white solids.

2.1a N-(2-chloro-pyrimidin-5-yl)-3-fluoro-benzamide (9)

$^1$H NMR (300 MHz, $d_6$-DMSO) δ 10.83 (s, 1H), 9.11 (s, 2H), 7.84 (d, J=7.9 Hz, 1H), 7.79–7.76 (m, 1H), 7.62 (q, J=8.0 Hz, 1H), 7.50 (dt, J=8.7, 2.6 Hz, 1H); $^{19}$F NMR (282 MHz, $d_6$-DMSO) δ −111.9 to −112.0 (m); $^{13}$C NMR (75 MHz, $d_6$-DMSO) δ 165.2, 162.4 (d, J=245.0 Hz), 154.2, 151.7, 136.1 (d, J=6.9 Hz), 134.2, 131.4 (d, J=8.1 Hz), 124.6 (d, J=2.9 Hz), 119.8 (d, J=20.7 Hz), 115.2 (d, J=23.6 Hz); MS(ESI): 249.7[M−H], 251.7[M−H].

2.1b 3-Chloro-N-(2-chloro-pyrimidin-5-yl)-benzamide (5)

$^1$H NMR (300 MHz, $d_6$-DMSO) δ 10.85 (s, 1H), 9.10 (s, 2H), 8.02 (s, 1H), 7.91 (dd, J=7.8, 1.2 Hz, 1H), 7.72–7.69 (m, 1H), 7.60 (dt, J=7.8, 0.9 Hz, 1H); $^{13}$C NMR (75 MHz, $d_6$-DMSO) δ 165.1, 154.1, 151.6, 135.8, 134.2, 133.9, 132.7, 131.2, 128.0, 127.2; MS(ESI): 265.7[M−H], 267.7[M−H], 269.6[M−H].

2.1c N-(2-chloro-pyrimidin-5-yl)-3-trifluoromethyl-benzamide (3)

$^1$H NMR (300 MHz, $d_6$-DMSO) δ 10.95 (s, 1H), 9.10 (s, 2H), 8.29 (s, 1H), 7.26 (d, J=7.8 Hz, 1H), 8.00 (d, J=7.7 Hz, 1H), 7.80 (t, J=7.8 Hz, 1H); $^{19}$F NMR (282 MHz, $d_6$-DMSO) δ −61.2; $^{13}$C NMR (75 MHz, d6-DMSO) δ 165.0, 154.2, 151.7, 134.8, 134.2, 132.5, 130.5, 129.8 (q, J=32.2 Hz), 129.4 (q, J=3.5 Hz), 124.8 (q, J=4.0 Hz), 124.4 (q, J=272.9 Hz); MS(ESI): 299.6[M−H], 301.6[M−H].

2.1d 4-Chloro-N-(2-chloro-pyrimidin-5-yl)-3-fluoro-benzamide (44)

$^1$H NMR (300 MHz, $d_6$-DMSO) δ 10.86 (s, 1H), 9.09 (s, 2H), 7.90 (d, J=9.4 Hz, 1H), 7.86–7.79 (m, 1H), 7.83 (s, 1H); $^{19}$F NMR (282 MHz, $d_6$-DMSO) δ −114.6 to −114.7 (m); $^{13}$C NMR (75 MHz, $d_6$-DMSO) δ 165.3, 162.4 (d, J=245.0 Hz), 154.2, 151.6, 134.7, 134.1, 131.6, 125.7, 124.4 (d, J=17.3 Hz), 116.7 (d, J=23.0 Hz); MS(ESI): 283.7[M−H], 285.7[M−H].

2.1e N-(2-Chloro-pyrimidin-5-yl)-3-fluoro-4-methyl-benzamide (90)

$^1$H NMR (300 MHz, $d_6$-DMSO) δ 10.73 (s, 1H), 9.10 (s, 2H), 7.73 (d, J=8.9 Hz, 2H), 7.48 (t, J=7.7 Hz, 1H), 2.31 (s, 3H); $^{19}$F NMR (282 MHz, $d_6$-DMSO) δ −115.7; $^{13}$C NMR (75 MHz, $d_6$-DMSO) δ 165.0, 161.4 (d, J=245.0 Hz), 154.0, 151.6, 134.3, 133.3 (d, J=6.5 Hz), 132.4 (d, J=5.2 Hz), 124.3, 114.7 (d, J=24.2 Hz), 14.8; MS(ESI): 263.7[M−H], 265.7[M−H].

2.1f 5-Chloro-thiophene-2-carboxylic acid (2-chloro-pyrimidin-5-yl)-amide (20)

$^1$H NMR (300 MHz, $d_6$-DMSO) δ 10.81 (s, 1H), 9.03 (s, 2H), 7.88 (d, J=4.2 Hz, 1H), 7.30 (d, J=4.0 Hz, 1H); $^{13}$C NMR (75 MHz, $d_6$-DMSO) δ 159.8, 154.1, 151.6, 137.8, 135.7, 133.8, 130.9, 129.1; MS(ESI): 272.0[M−H], 274.0[M−H].

2.1g N-(2-Chloro-pyrimidin-5-yl)-3,4-difluoro-benzamide (4)

$^1$H NMR (300 MHz, $d_6$-DMSO) δ 10.80 (s, 1H), 9.08 (s, 2H), 8.04–7.98 (m, 1H), 7.88–7.86 (m, 1H), 7.63 (q, J=8.4Hz, 1H); $^{19}$F NMR (282 MHz, $d_6$-DMSO) δ −132.1 to −132.3 (m), −136.8 to −136.9 (m); $^{13}$C NMR (75 MHz, $d_6$-DMSO) δ 164.2, 154.2, 152.6 (dd, J=213.0, 11.7 Hz), 151.6, 149.4 (dd, J=208.4, 12.7 Hz), 134.1, 131.2 (t, J=3.5 Hz), 126.0 (dd, J=8.1, 3.5 Hz), 118.4 (d, J=17.8 Hz), 117.8 (d, J=19 Hz); MS(ESI): 267.8[M−H], 269.8[M−H].

2.2 Alternate Method When X=Cl

2.2a Preparation of 2-hydroxy-5-nitropyrimidine

With reference to Scheme 3, to a solution of 2800 g (21.13 mol) of 2-hydroxypyrimidine hydrochloride in 8400 mL of concentrated sulfuric acid was added dropwise 3434 g (52.83 mol) of fuming nitric acid. The solution was heated at reflux for 16 h, then it was allowed to cool to room temperature and was poured slowly into cold water (30 L). The mixture was basified with 50% NaOH to pH 2.5. Isopropyl alcohol (16 L) was added and the mixture was stirred for 60 minutes after which the layers were allowed to separate. The organic layer was diluted with ethyl acetate (16 L) and washed with brine. The organics were concentrated under reduced pressure to yield 2689 g of crude product, which was used in the next step without purification.

2.2b Preparation of 2-hydroxy-5-nitropyrimidine

A mixture of 2689 g of crude 2-hydroxy-5-nitropyrimidine (X) and $POCl_3$ (12 L) were heated at reflux for 2 h. The reaction was concentrated under reduced pressure to approximately 20% of its original volume and allowed to cool overnight. The resulting slurry was diluted with dichloromethane (2000 mL) and poured slowly into water (20 L) while keeping the temperature below 15° C. To the cloudy suspension was added ethyl acetate (12 L) and the layers were allowed to partition. The aqueous layer was extracted with ethyl acetate (12 L). The combined organics were dried over magnesium sulfate, filtered and concentrated under reduced pressure to yield 1126 g (33.2% over 2 steps) of the desired product as a yellow solid.

2.2c Preparation of 5-amino-2-chloropyrimidine

To a mixture of 914 g (16.4 mol) of iron in warm acetic acid (2 L, 45° C.) was added a solution of 2-chloro-5-nitropyrimidine in THF (6 L). The 2-chloro-5-nitropyrimidine was added at a rate (over approx. 2.5 h) that kept the temperature of the reaction mixture below 60° C. The reaction was complete upon completion of addition and was concentrated under reduced pressure. To the crude solids was added ethyl acetate (6 L) and the dissolved product was purified on a silica plug, eluting the desired material with ethyl acetate. The ethyl acetate fractions were pooled and concentrated under reduced pressure to yield 435 g (58.1%) of a yellow solid.

2.2d Preparation of N-(2-chloropyrimidin-5-yl)-3,4-difluorobenzamide

A solution of 450 g (3.49 mol) of 5-amino-2-chloropyrimidine and 790 g (6.98 mol) of triethylamine in anhydrous THF was cooled to less than 5° C. in an ice bath. To this solution was added 3,4-difluorobenzoyl chloride at a rate (2 h) that maintained the temperature of the reaction mixture below 10° C. Once the addition was complete the reaction was monitored for full conversion of the starting material to product by HPLC. Following confirmation of complete conversion, the reaction mixture was concentrated under reduced pressure. The viscous residue was dissolved in ethyl acetate (4 L) and washed with water (4 L) and 2M HCl (4 L). The organic layer was separated, dried over magnesium sulfate, filtered and concentrated under reduced pressure. The resulting solid was dissolved in ethanol (4 L) and 250 g of charcoal was added. The mixture was heated to reflux for 10 minutes and filtered through a bed of Celite® and the filtrate was concentrated under reduced pressure. The solids were recrystallized twice from acetonitrile (1 L) to yield 580 g (61.8%) of the desired product as an off-white solid.

2.2 General Method When X=OH

Oxalyl chloride (1.2 eq) was added to a suspension of acid chloride (1.2 eq) and DMF (catalytic amount) in DCM at rt. After 1 h the resulting solution was added to a solution of 2-chloro-pyrimidin-5-ylamine (1 eq) and pyridine (3 eq) in THF (0.2 M) at rt. After a further 1 h the solvent was removed under reduced pressure. Purification of the crude material by column chromatography (hexanes/EtOAc) gave the desired products in high yields (>80%) typically as white solids.

Example 3

Preparation of 3,4-difluoro-N-(2-methyl-pyrimidin-5-yl)-benzamide (8)

A mixture of trimethylboroxine (27 μL, 0.19 mmol), Pd(dppf)$_2$Cl$_2$ (22 mg, 0.019 mmol), Cs$_2$CO$_3$ (185 mg, 0.57 mmol) and N-(2-chloro-pyrimidin-5-yl)-3,4-difluoro-benzamide (H) (50 mg, 0.19 numol) in dioxane (1 mL)/H$_2$O (0.1 mL) was heated at 110–130° C. (bath temperature) for 1 h. The crude reaction mixture was filtered through a pad of celite and concentrated under reduced pressure. Purification of the crude material by column chromatography (hexanes/EtOAc) gave the desired product as white solid (27 mg, 57%).

$^1$H NMR (300 MHz, d$_6$-DMSO) δ 10.59 (s, 1H), 9.00 (s, 2H), 8.04 (ddd, J=10.1, 7.6, 1.9 Hz, 1H), 7.88–87 (m, 1H), 7.70–7.63 (m, 1H), 2.58 (s, 3H); $^{19}$F NMR (282 MHz, d$_6$-DMSO) δ −132.6 to −132.7 (m), −136.9 to −137.1 (m); MS(ESI): 248.1[M−H].

Example 4

Preparation of Compound 91

A capped scintillation vial containing a mixture of 158 mg (1.0 mmol) of 3,4-difluorobenzoic acid, 186 μL (2.0 mmol) of 2-propanethiol and 652 mg (2.0 mmol) of cesium carbonate in 2.5 mL of DMSO was heated at 50 C for 2.5 days. The reaction mixture was cooled to room temperature and partitioned between ethyl ether and 1M HCl. The organic phase was separated and washed with water and brine. The organic layer was dried (MgSO$_4$) and concentrated in vacuo. The concentrated material was dissolved in 6 mL of THF and treated with a solution of 0.52 g (2.0 mmol) of 3-chloroperoxybenzoic acid (66% by weight) in 4 mL of DCM. The reaction mixture was stirred at rt overnight and then concentrated in vacuo. The residue was dissolved in 5% methanol/CHCl$_3$ and absorbed onto SiO$_2$. Chromatography on SiO$_2$ (5% to 7% methanol/CHCl$_3$) afforded 204 mg (83% yield) of 3-fluoro-4-(propane-2-sulfonyl)-benzoic acid as a white solid.

A solution of 24.6 mg (0.10 mmol) of 3-fluoro-4-(propane-2-sulfonyl)-benzoic acid in 1.0 mL of DCM was treated with 9 μL (0.10 mmol) of oxalyl chloride and a drop of DMF. The solution was stirred at rt for 1 h and then concentrated in vacuo. The residue was dissolved in 0.5 mL of THF and treated with 10 μL (0.12 mmol) of pyridine and a solution of 16 mg (0.12 mmol) of 5-amino-2-chloropyrimidine in 0.5 mL of CH$_3$CN. The reaction mixture was stirred at room temperature overnight and then concentrated in vacuo. The residue was partitioned between EtOAc and 1M NaH$_2$PO$_4$ solution. The organic phase was washed with brine, dried (Na$_2$SO$_4$), and concentrated in vacuo. Chromatography on SiO$_2$ afforded 20 mg (56% yield) of N-(5-amino-2-chloro-pyrimidine)-3-fluoro-4-(propane-2-sulfonyl)-benzamide, 91, as a white solid.

Example 5

This example illustrates screening protocols for evaluating putative potassium channel agonists for the ability to open voltage-gated potassium channels.

NG108-15 cells, a mouse neuroblastoma, rat glioma hybrid cell line, functionally express M-currents (Robbins et al., *J. Physiol.* 451: 159–85 (1992). NG108-15 M-currents are likely comprised, at least in part, of KCNQ2, KCNQ3 and KCNQ5, since these genes are reportedly robustly expressed in differentiated NG108-15 cells (Selyanko et al., *J. Neurosci.* 19(18): 7742–56 (1999); Schroeder et al., *J. Biol. Chem.* 275(31): 24089–95 (2000)) and KCNQ3 dominant- negative constructs reduce M-current density in these cells (Selyanko et al., *J. Neurosci.* 22(5): RC212 (2002).

NG108–15 are maintained in DMEM (high glucose) supplemented with 10% fetal bovine serum, 0.05 mM pyridoxine, 0.1 mM hypoxanthine, 400 nM aminopterin, 16 mM thymidine, 50 μgml$^{-1}$ gentamycin and 10 mM HEPES, in an incubator at 37° C. with a humidified atmosphere of 5% CO$_2$. Cells are plated in 96 well plates and are differentiated by addition of 10 μM PGE1 and 50 μM isomethylbutylxanthine to the growth media prior to study.

Differentiated NG108–15 cells are loaded with voltage-sensitive dye by incubation in Earls Balanced Salt Solution (EBSS) containing 5 mM DiBAC for 1 h. Following loading, drug solution containing 5 mM DiBAC is added to each well. Changes in fluorescence are measured every 30 s for 25 min. The maximum change in fluorescence is measured and can be expressed as a percentage of the maximum response obtained in the presence of a positive control agent.

Alternatively, cells expressing voltage-gated K$^+$ channels, such as KCNQ2-like channels can be loaded with $^{86}$Rb$^+$ by culture in media containing $^{86}$RbCl. Following loading, culture media is removed and the cells are washed in EBSS to remove residual traces of $^{86}$Rb$^+$. Cells are preincubated with drug (0.01–30 μM in EBSS) and then $^{86}$Rb$^+$ efflux is stimulated by exposing cells to EBSS solution supplemented with a sub-maximal concentration of KCl (generally 7–20 mM) in the continued presence of drug. After a suitable efflux period, the EBSS/KCl solution is removed from the cells and the $^{86}$Rb$^+$ content can be determined by Cherenkov counting (Wallac Trilux). Cells are then lysed with a SDS solution and the $^{86}$Rb$^+$ content of the lysate can be determined. Percent $^{86}$Rb$^+$ efflux is calculated according to:

($^{86}$Rb$^+$ content in EBSS/($^{86}$Rb$^+$ content in EBSS+ $^{86}$Rb$^+$ content of the lysate))*100

Efflux is normalized to the maximal $^{86}$Rb$^+$ efflux (i.e., that which can be induced by a high concentration of KCl, generally 30–135 mM).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

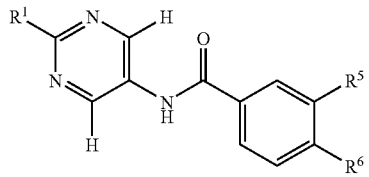

in which,

R$^1$, R$^5$, and R$^6$ are independently selected from halogen.

2. The compound according to 1, wherein R$^5$ and R$^6$ are F.

3. The compound according to 1, wherein R$^1$ is Cl.

4. A compound having the formula:

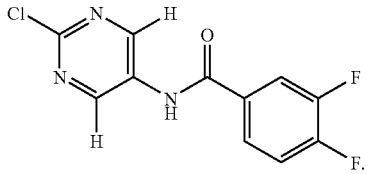

5. A method of treating epilepsy through modulation of a voltage-dependent potassium channel, said method comprising administering to a subject in need of such treatment, an effective amount of a compound having the formula:

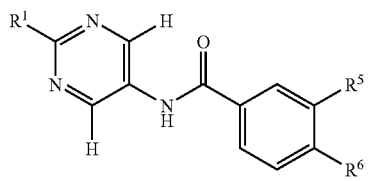

in which,

R$^1$, R$^5$, and R$^6$ are independently selected from halogen.

6. The method according to 5, wherein R$^5$ and R$^6$ are F.

7. The method according to 5, wherein R$^1$ is Cl.

8. A method of treating epilepsy through modulation of a voltage-dependent potassium channel, said method comprising administering to a subject in need of such treatment, an effective amount of a compound having the formula:

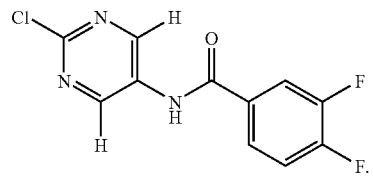

9. A composition comprising a pharmaceutically acceptable excipient and a compound of the formula:

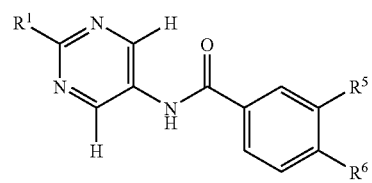

in which,

R, R$^5$, and R$^6$ are independently selected from halogen.

10. The composition according to 9, wherein R$^5$ and R$^6$ are F.

11. The composition according to 9, wherein R$^1$ is Cl.

12. A composition comprising a pharmaceutically acceptable excipient and a compound of the formula:

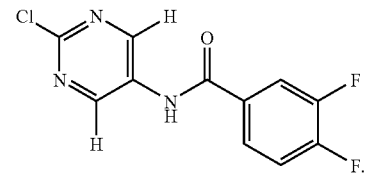

13. A compound selected from the group consisting of:

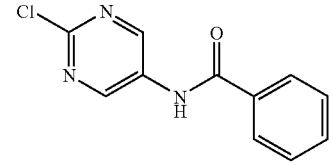

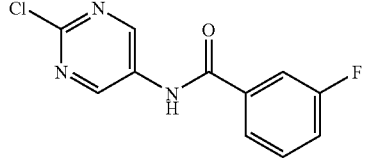

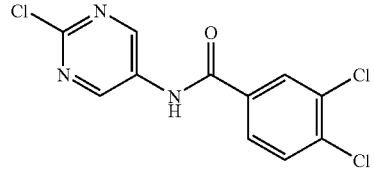

-continued
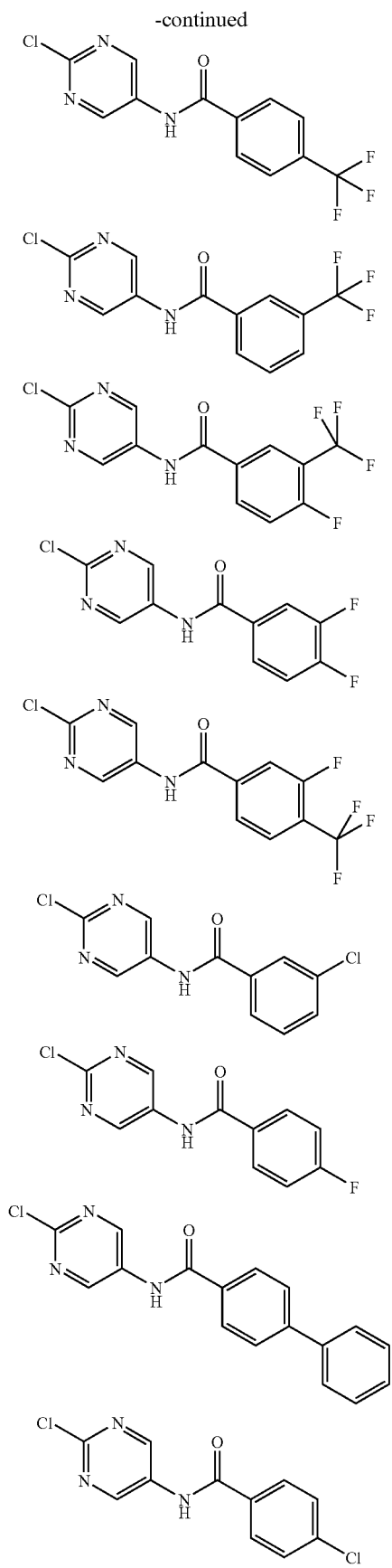
-continued
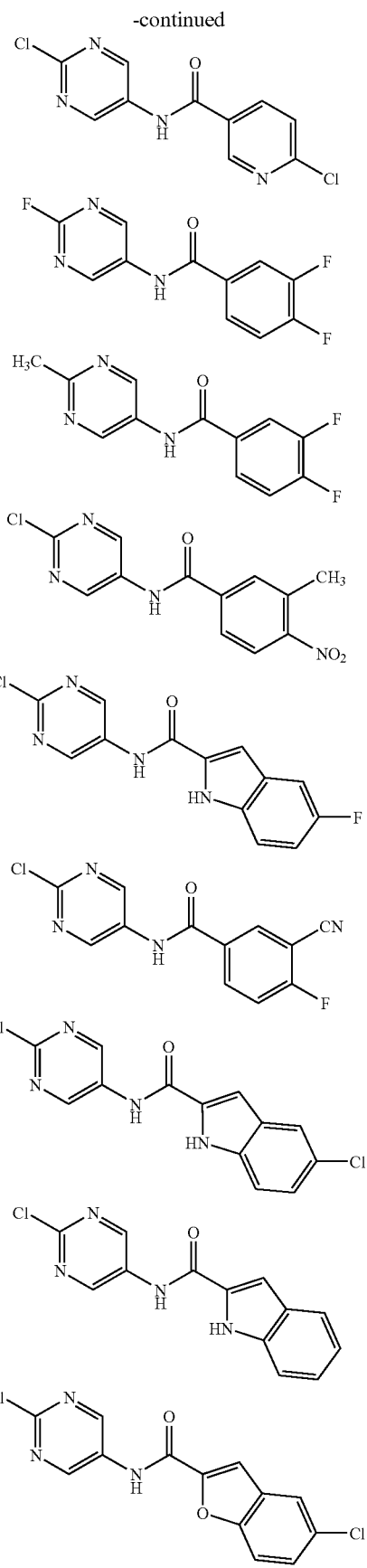

-continued
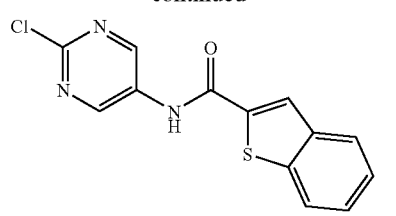
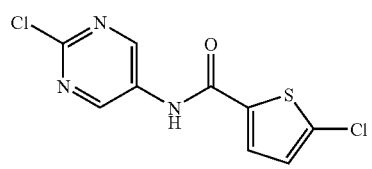
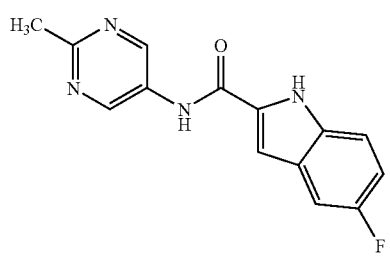
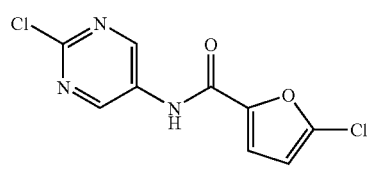
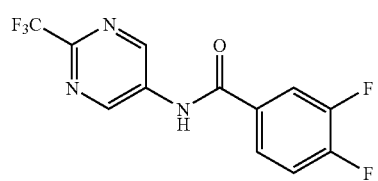
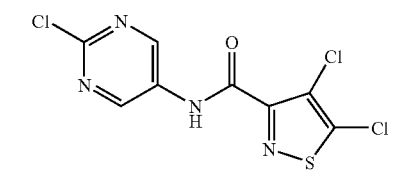
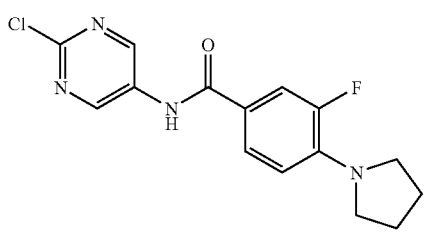
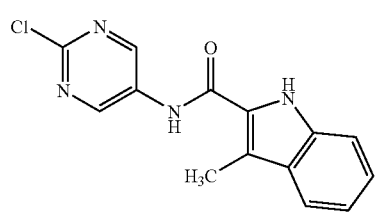
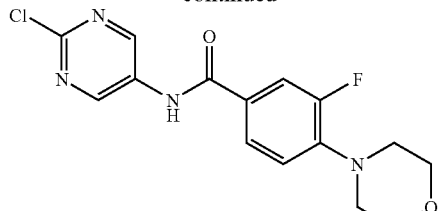
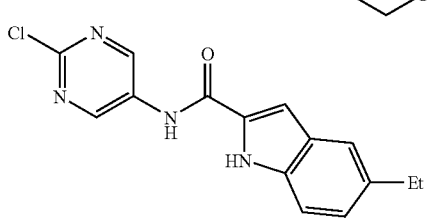
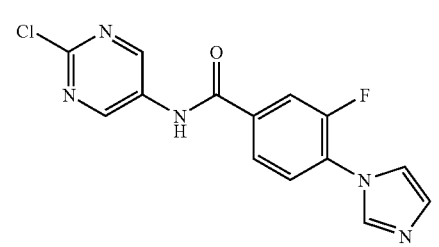
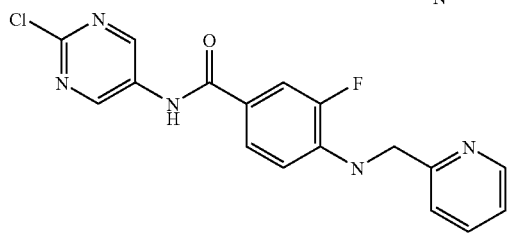
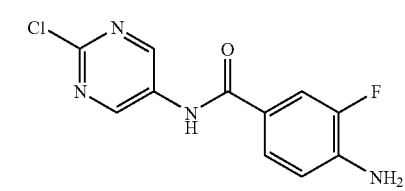
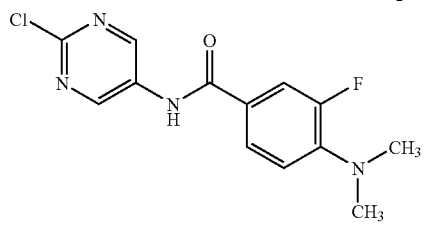
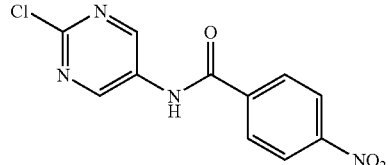
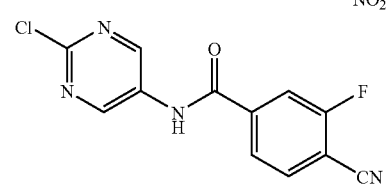

-continued
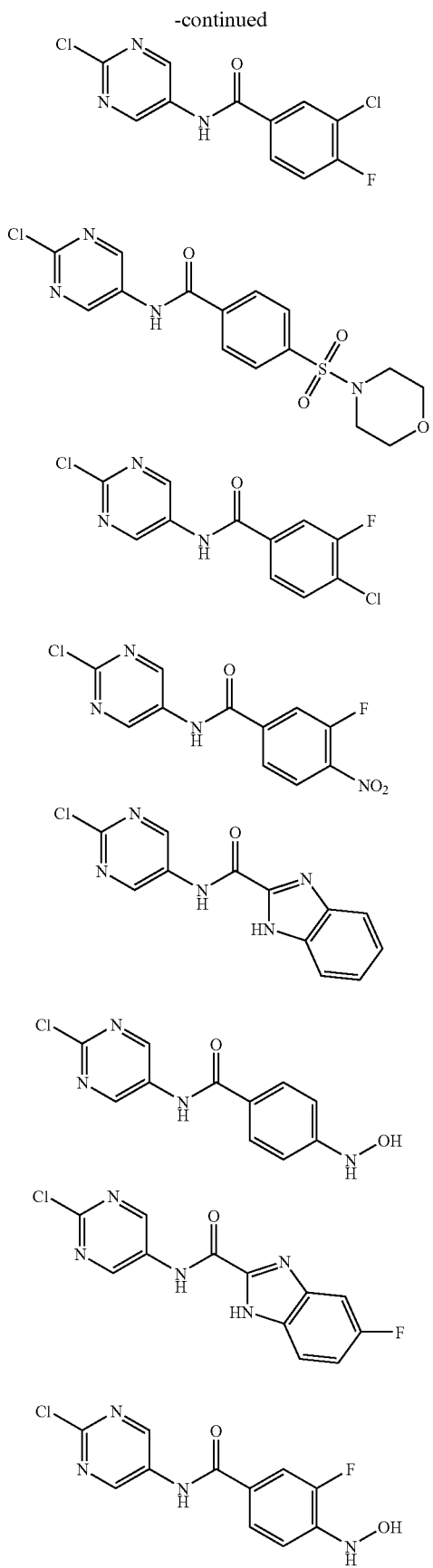
-continued
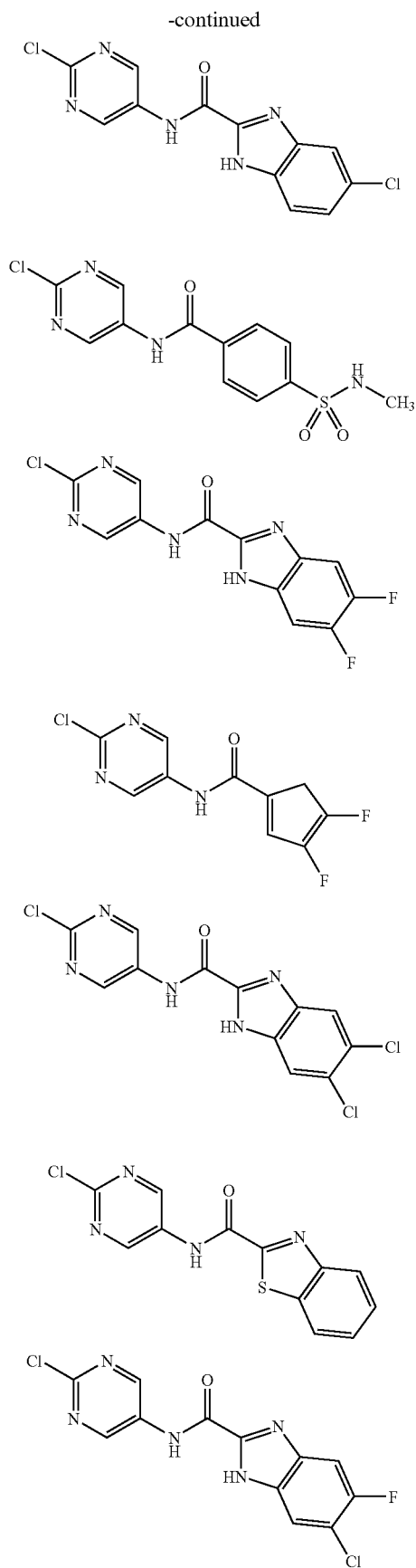

-continued
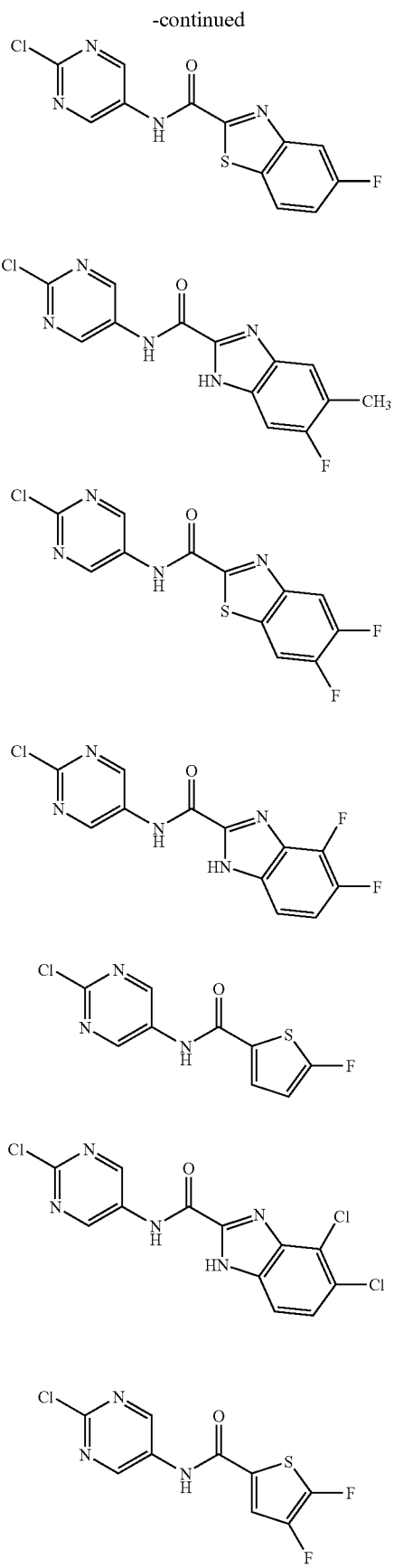
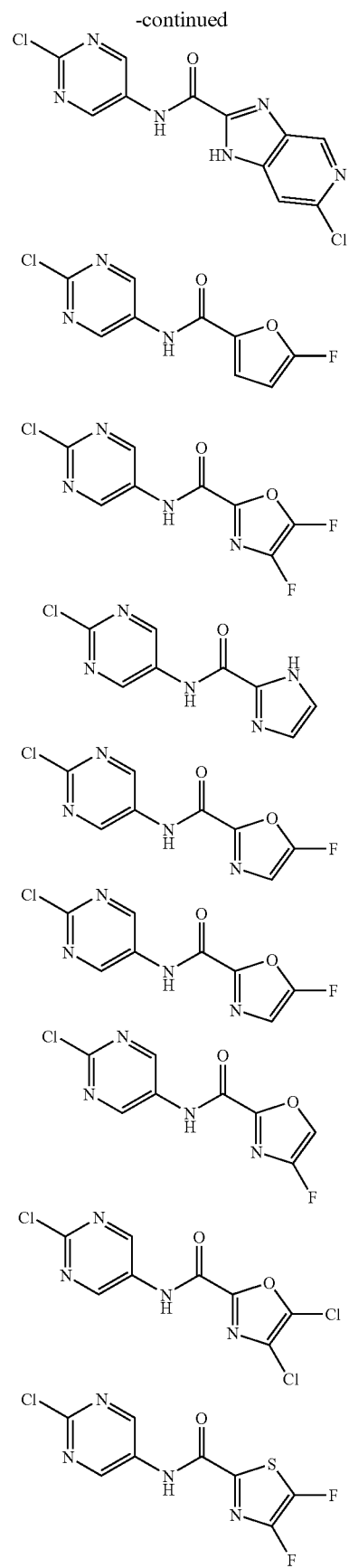

-continued
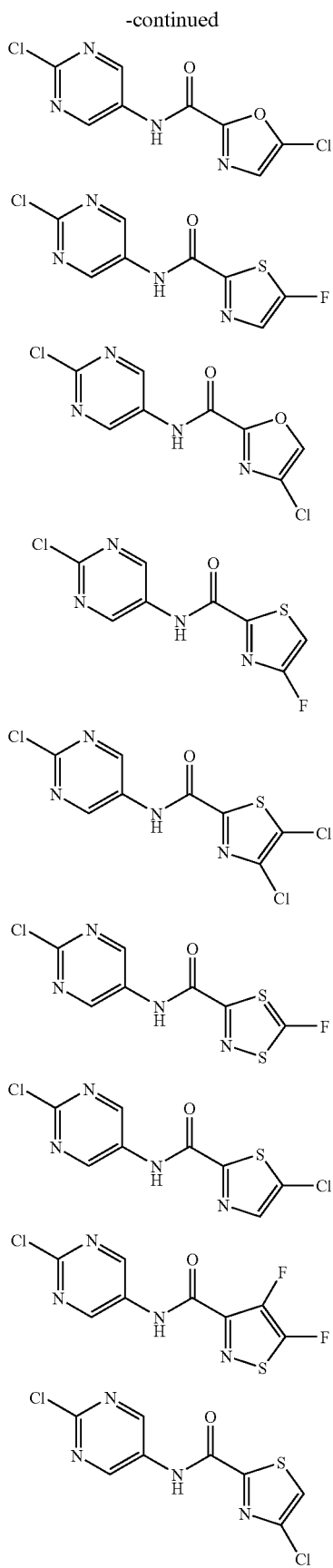
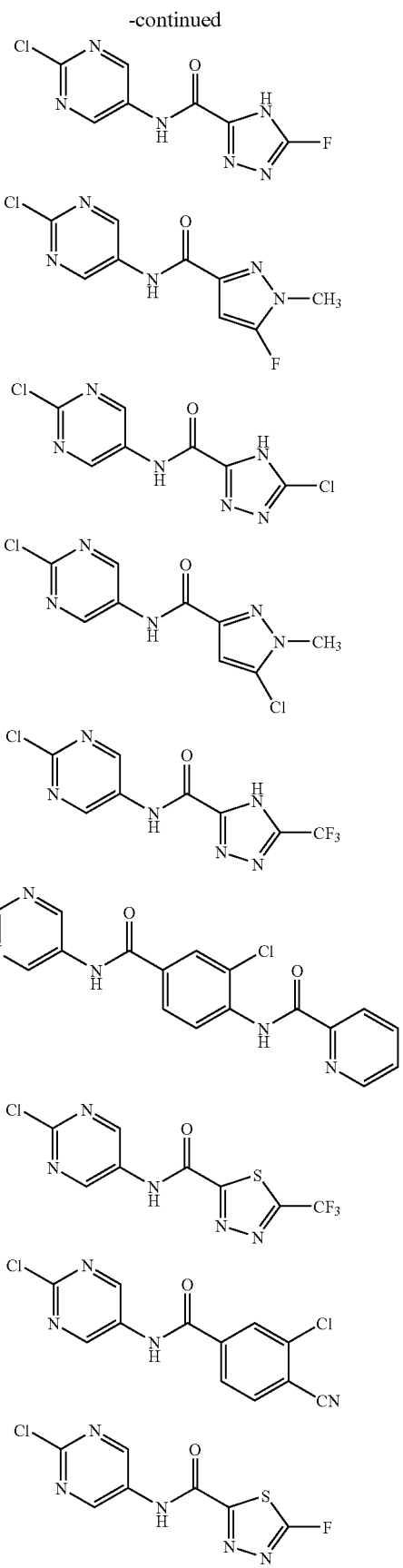

-continued
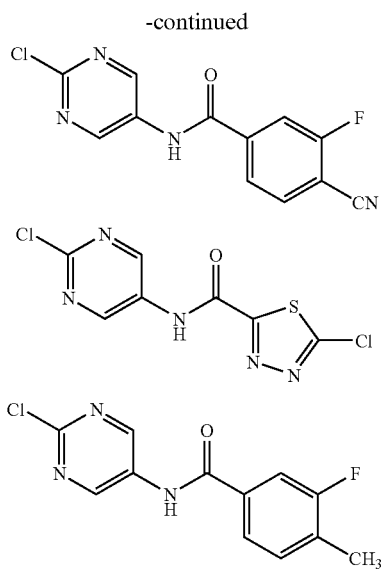
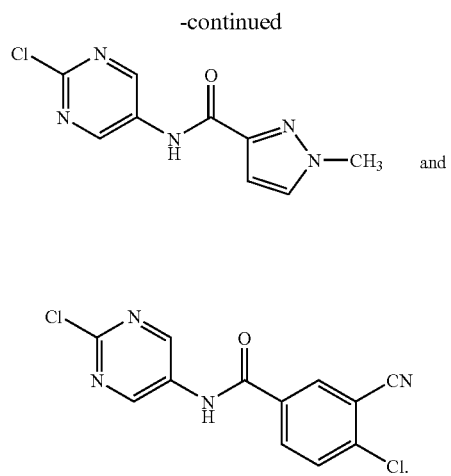
and
* * * * *